US008791144B2

(12) United States Patent
Macdonald et al.

(10) Patent No.: US 8,791,144 B2
(45) Date of Patent: Jul. 29, 2014

(54) SUBSTITUTED N-PHENYL-1-(4-PYRIDINYL)-1H-PYRAZOL-3-AMINES

(75) Inventors: Gregor James Macdonald, Beerse (BE); Johannes Wilhelmus John F. Thuring, Antwerp (BE); Frans Alfons Maria Van den Keybus, Beerse (BE); Yves Emiel Maria Van Roosbroeck, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 59 days.

(21) Appl. No.: 13/496,120

(22) PCT Filed: Sep. 16, 2010

(86) PCT No.: PCT/EP2010/063609

§ 371 (c)(1), (2), (4) Date: Mar. 14, 2012

(87) PCT Pub. No.: WO2011/033018

PCT Pub. Date: Mar. 24, 2011

(65) Prior Publication Data

US 2012/0172354 A1 Jul. 5, 2012

(30) Foreign Application Priority Data

Sep. 17, 2009 (EP) .................................... 09170525

(51) Int. Cl.
*A61K 31/4439* (2006.01)
*C07D 401/04* (2006.01)

(52) U.S. Cl.
USPC ........................................ 514/341; 546/275.4

(58) Field of Classification Search
USPC ........................................ 546/275.4; 514/341
See application file for complete search history.

(56) References Cited

FOREIGN PATENT DOCUMENTS

| | | | |
|---|---|---|---|
| EP | 0248523 | B1 | 10/1991 |
| WO | 2005051917 | A1 | 6/2005 |
| WO | 2006064375 | A2 | 6/2006 |
| WO | 2007118903 | A1 | 10/2007 |
| WO | WO2007118903 | A1 | 10/2007 |
| WO | 2009135944 | A1 | 11/2009 |

OTHER PUBLICATIONS

Yu et al., "Physical characterization of, etc.," PSTT, vl. 1(3), 118-127 (1998).*

Kirk-Othmer Encyclopedia of Chemical Technology, 8, pp. 95-147 (2002).*

Vippagunta et al., "Crystalline Solids", Advanced Drug Delivery Reviews 48 (2001) 3-26.*

Guillory (in Brittain ed.), "Polymorphism in Pharmaceutical Solids.," NY: Marcel Dekker, Inc., 1999, 1-2, 125-181, 183-226.*

Jain et al., "Polymorphism in Pharmacy", Indian Drugs, 1986, 23(6) 315-329.*

* cited by examiner

*Primary Examiner* — Patricia L Morris
(74) *Attorney, Agent, or Firm* — Peter L. Herridge

(57) ABSTRACT

The present invention relates to N-phenyl-1-(4-pyridinyl)-1H-pyrazol-3-amine derivatives and pharmaceutically acceptable salts thereof, processes for preparing them, pharmaceutical compositions containing them and their use in therapy, according to formula (I)

(I)

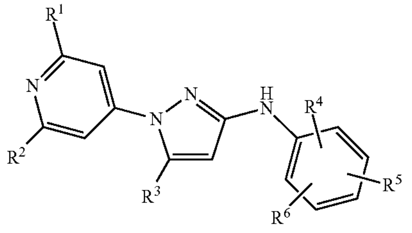

Wherein $R^1$, $R^2$, $R^3$, $R^4$, $R^5$, $R^6$ have the meaning defined in the claims.

The invention particularly relates to positive allosteric modulators of nicotinic acetylcholine receptors, such positive allosteric modulator having the capability to increase the efficacy of nicotinic receptor agonists.

6 Claims, No Drawings

SUBSTITUTED N-PHENYL-1-(4-PYRIDINYL)-1H-PYRAZOL-3-AMINES

This application is a national stage application of PCT/EP2010/063609, filed Sep. 16, 2010, which claims priority benefit of Application No. EP 09170525.1 filed Sep. 17, 2009. The complete disclosures of the aforementioned related patent applications are hereby incorporated herein by reference for all purposes.

The present invention relates to N-phenyl-1-(4-pyridinyl)-1H-pyrazol-3-amine derivatives and pharmaceutically acceptable salts thereof, processes for preparing them, pharmaceutical compositions containing them and their use in therapy. The invention particularly relates to positive allosteric modulators of nicotinic acetylcholine receptors, such positive allosteric modulators having the capability to increase the efficacy of nicotinic receptor agonists.

BACKGROUND PRIOR ART

W0-2007/118903 discloses 1-alkyl-3-aniline-5-aryl-1,2,4-triazoles as positive modulators of nicotinic acetylcholine receptors useful for treating neurological, degenerative and psychiatric disorders.

WO-2005/051917 discloses pyrazolyl derivatives in the form of drugs for treating acute or chronic neuronal regressions.

WO-2009/135944 discloses 1-alkyl-3-aniline-5-aryl-pyrazole derivatives as positive allosteric modulators of nicotinic acetylcholine receptors.

EP-0,248,523 discloses N-[4-methoxyphenyl)-1-methyl-5-phenyl-1H-pyrazol-3-amine useful as a broad spectrum anti-inflammatory agent.

BACKGROUND OF THE INVENTION

Cholinergic receptors normally bind the endogenous neurotransmitter acetylcholine (ACh), thereby triggering the opening of ion channels. ACh receptors in the mammalian central nervous system can be divided into muscarinic (mAChR) and nicotinic (nAChR) subtypes based on the agonist activities of muscarine and nicotine, respectively. The nicotinic acetylcholine receptors are ligand-gated ion-channels containing five subunits. Members of the nAChR subunit gene family have been divided into two groups based on their amino acid sequences; one group containing so-called β subunits, and a second group containing α subunits. Three kinds of α subunits, α7, α8 and α9, have been shown to form functional receptors when expressed alone and thus are presumed to form homooligomeric pentameric receptors.

An allosteric transition state model of the nAChR has been developed that involves at least a resting state, an activated state and a "desensitized" closed channel state, a process by which receptors become insensitive to the agonist. Different nAChR ligands can stabilize the conformational state of a receptor to which they preferentially bind. For example, the agonists ACh and (−)-nicotine respectively stabilize the active and desensitized states.

Changes of the activity of nicotinic receptors have been implicated in a number of diseases. Some of these, for example myasthenia gravis and autosomal dominant nocturnal front lobe epilepsy (ADNFLE) are associated with reductions in the activity of nicotinic transmission either because of a decrease in receptor number or increased desensitization.

Reductions in nicotinic receptors have also been hypothesized to mediate cognitive deficits seen in diseases such as Alzheimer's disease and schizophrenia.

The effects of nicotine from tobacco are also mediated by nicotinic receptors and since the effect of nicotine is to stabilize receptors in a desensitized state, an increased activity of nicotinic receptors may reduce the desire to smoke.

Compounds which bind nAChRs have been suggested for the treatment of a range of disorders involving reduced cholinergic function such as learning deficit, cognition deficit, attention deficit and memory loss. Modulation of α7 nicotinic receptor activity is expected to be beneficial in a number of diseases including Alzheimer's disease, Lewy Body Dementia, Attention Deficit Hyperactivity Disorder, anxiety, schizophrenia, mania, bipolar disorder, Parkinson's disease, Huntington's disease, Tourette's syndrome, brain trauma and other neurological, degenerative and psychiatric disorders in which there is loss of cholinergic synapses, including jetlag, nicotine addiction, and pain.

However, treatment with nicotinic receptor agonists which act at the same site as ACh is problematic because ACh not only activates, but also blocks receptor activity through processes which include desensitization and uncompetitive blockade. Furthermore, prolonged activation appears to induce a long-lasting inactivation. Therefore, agonists of ACh can be expected to reduce activity as well as enhance it.

At nicotinic receptors in general, and of particular note at the α7-nicotinic receptor, desensitization limits the duration of action of an applied agonist.

DESCRIPTION OF THE INVENTION

We have found that certain novel pyrazole derivatives can increase the efficacy of agonists at nicotinic acetylcholine receptors (nAChR). Compounds having this type of action (hereinafter referred to as "positive allosteric modulators") are likely to be useful for treatment of conditions associated with reductions in nicotinic transmission. In a therapeutic setting such compounds could restore normal interneuronal communication without affecting the temporal profile of activation. In addition, positive allosteric modulators are not expected to produce long-term inactivation of receptors as may occur with prolonged application of agonists.

Positive nAChR modulators of the present invention are useful for treatment and prophylaxis of psychotic disorders, intellectual impairment disorders and diseases, inflammatory diseases and conditions in which modulation of the α7 nicotinic receptor is beneficial.

The present invention concerns N-phenyl-1-(4-pyridinyl)-1H-pyrazol-3-amine derivatives having positive allosteric modulator properties, in particular increasing the efficacy of agonists at the α7 nicotinic receptor. In view of the aforementioned pharmacology of the present derivatives, it follows that they may be suitable for use as a medicament. The invention further relates to methods for their preparation and pharmaceutical compositions comprising them. The invention also relates to the use of these derivatives for the manufacture of a medicament for the treatment and prophylaxis of psychotic disorders, intellectual impairment disorders and diseases, inflammatory diseases and conditions in which modulation of the α7 nicotinic receptor is beneficial. The invention also relates to these derivatives for use in treating and preventing psychotic disorders, intellectual impairment disorders and diseases, inflammatory diseases and conditions in which modulation of the α7 nicotinic receptor is beneficial.

There is a strong need for novel positive allosteric modulators having the capability to increase the efficacy of nicotinic receptor agonists thereby opening new avenues for the treatment of psychotic disorders, intellectual impairment disorders, or inflammatory diseases. It is an object of the present invention to overcome or ameliorate at least one of the disadvantages of the prior art, or to provide a useful alternative. It is accordingly an object of the present invention to provide such novel compounds.

The compounds of the present invention differ structurally from the prior art compounds.

The present invention relates to novel compounds according to formula (I)

(I)

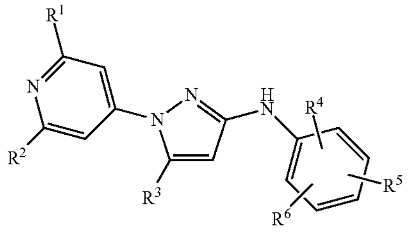

and stereoisomeric forms thereof, wherein $R^1$ and $R^2$ each independently represent hydrogen or $C_{1-4}$alkyl;

$R^3$ is $C_{1-6}$alkyl optionally substituted with one or more substituents independently selected from the group consisting of hydroxyl, cyano, $C_{1-6}$alkyloxy, benzyloxy, $R^xR^yN$—C(═O)—, and $R^zO$—C(═O)—;

$R^x$ and $R^y$ each independently represent hydrogen, $C_{1-4}$alkyl, cyclo$C_{3-6}$alkyl or (cyclo$C_{3-6}$alkyl)$C_{1-4}$alkyl;

$R^z$ represents hydrogen or $C_{1-3}$alkyl;

$R^4$, $R^5$ and $R^6$ each independently represent hydrogen, halo, $C_{1-6}$alkyl, cyano, trifluoromethyl, trifluoromethoxy, or methoxy; or $R^4$ and $R^5$ when attached to 2 vicinal carbon atoms together form a bivalent radical of formula —O—$CF_2$—O—;

and the pharmaceutically acceptable addition salts, and the hydrates and the solvates thereof.

It will be appreciated that some of the compounds according to formula (I) and the addition salts, hydrates and solvates thereof may contain one or more centers of chirality and exist as stereoisomeric forms.

The present invention will now be further described. In the following passages, different aspects of the invention are defined in detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

The term "halo" as a group or part of a group is generic for fluoro, chloro, bromo, iodo unless otherwise is indicated or is clear from the context.

The term "$C_{1-6}$alkyl" as a group or part of a group refers to a hydrocarbyl radical of Formula $C_nH_{2n+1}$ wherein n is a number ranging from 1 to 6. $C_{1-6}$alkyl groups comprise from 1 to 6 carbon atoms, in particular from 1 to 4 carbon atoms, more in particular from 1 to 3 carbon atoms, even more in particular 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-6}$alkyl includes all linear, or branched alkyl groups with between 1 and 6 carbon atoms, and thus includes such as for example methyl, ethyl, n-propyl, i-propyl, 2-methyl-ethyl, butyl and its isomers (e.g. n-butyl, isobutyl and tert-butyl), pentyl and its isomers, hexyl and its isomers, and the like.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, in particular from 1 to 3 carbon atoms, more in particular 1 to 2 carbon atoms. $C_{1-4}$alkyl includes all linear, or branched alkyl groups with between 1 and 4 carbon atoms, and thus includes such as for example methyl, ethyl, n-propyl, 2-methyl-ethyl, butyl and its isomers (e.g. n-butyl, isobutyl and tert-butyl), and the like.

The term "$C_{1-3}$alkyl" as a group or part of a group refers to a hydrocarbyl radical of Formula $C_nH_{2n+1}$ wherein n is a number ranging from 1 to 3. $C_{1-3}$alkyl groups comprise from 1 to 3 carbon atoms, preferably from 1 to 2 carbon atoms. $C_{1-3}$alkyl includes all linear, or branched alkyl groups with between 1 and 3 carbon atoms, and thus includes such as for example methyl, ethyl, n-propyl, i-propyl, 2-methyl-ethyl and its isomers, and the like.

The term "$C_{1-6}$alkyloxy" as a group or part of a group refers to a radical having the Formula $OR^a$ wherein $R^a$ is $C_{1-6}$alkyl. Non-limiting examples of suitable alkyloxy include methyloxy, ethyloxy, propyloxy, isopropyloxy, butyloxy, isobutyloxy, sec-butyloxy, tert-butyloxy, pentyloxy, and hexyloxy.

The term "cyclo$C_{3-6}$alkyl" alone or in combination, refers to a cyclic saturated hydrocarbon radical having from 3 to 6 carbon atoms. Non-limiting examples of suitable cyclo$C_{3-6}$ alkyl include cyclopropyl, cyclobutyl, cyclopentyl and cyclohexyl.

The chemical names of the compounds of the present invention were generated according to the nomenclature rules agreed upon by the Chemical Abstracts Service, using Advanced Chemical Development, Inc., nomenclature software (ACD/Name product version 10.01; Build 15494, 1 Dec. 2006).

Some of the compounds according to formula (I) may also exist in their tautomeric form. Such forms although not explicitly indicated in the above formula are intended to be included within the scope of the present invention.

When any variable occurs more than one time in any constituent, each definition is independent.

It will be appreciated that some of the compounds of Formula (I) and their pharmaceutically acceptable addition salts and stereoisomeric forms may contain one or more centers of chirality and exist as stereoisomeric forms.

The term "stereoisomeric forms" as used hereinbefore or hereinafter defines all the possible stereoisomeric forms which the compounds according to formula (I) and their addition salts may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms according to formula (I) and their salts, solvates, substantially free, i.e. associated with less than 10%, preferably less than 5%, in particular less than 2% and most preferably less than 1% of the other isomers.

For therapeutic use, salts of the compounds according to formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds according to formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvates comprises the solvent addition forms which the compounds according to formula (I) as well as the salts thereof, may form. Examples of such forms are e.g. alcoholates and the like.

The compounds of Formula (I) as prepared in the processes described below may be synthesized in the form of racemic mixtures of enantiomers that can be separated from one another following art-known resolution procedures. A manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reactions occur with retention of stereochemical integrity. Preferably if a specific stereoisomer is desired, said compound would be synthesized by stereospecific methods of preparation. These methods will advantageously employ enantiomerically pure starting materials.

In the framework of this application, a compound according to the invention is inherently intended to comprise all isotopic combinations of its chemical elements. In the framework of this application, a chemical element, in particular when mentioned in relation to a compound according to formula (I), comprises all isotopes and isotopic mixtures of this element. For example, when hydrogen is mentioned, it is understood to refer to $^{1}H$, $^{2}H$, $^{3}H$ and mixtures thereof.

A compound according to the invention therefore inherently comprises a compound with one or more isotopes of one or more element, and mixtures thereof, including a radiolabelled compound, wherein one or more non-radioactive atoms has been replaced by one of its radioactive isotopes. By the term "radiolabelled compound" is meant any compound according to formula (I), or a pharmaceutically acceptable salt thereof, which contains at least 1 radioactive atom. For example, a compound can be labelled with positron or with gamma emitting radioactive isotopes. For radioligand-binding techniques, the $^{3}H$-atom or the $^{125}I$-atom is the atom of choice to be replaced. For imaging, the most commonly used positron emitting (PET) radioactive isotopes are $^{11}C$, $^{18}F$, $^{15}O$ and $^{13}N$, all of which are accelerator produced and have half-lives of 20, 100, 2 and 10 minutes (min) respectively. Since the half-lives of these radioactive isotopes are so short, it is only feasible to use them at institutions which have an accelerator on site for their production, thus limiting their use. The most widely used of these are $^{18}F$, $^{99m}Tc$, $^{201}Tl$ and $^{123}I$. The handling of these radioactive isotopes, their production, isolation and incorporation in a molecule are known to the skilled person.

In particular, the radioactive atom is selected from the group of hydrogen, carbon, nitrogen, sulfur, oxygen and halogen. In particular, the radioactive isotope is selected from the group of $^{3}H$, $^{11}C$, $^{18}F$, $^{122}I$, $^{123}I$, $^{125}I$, $^{131}I$, $^{75}Br$, $^{76}Br$, $^{77}Br$ and $^{82}Br$.

As used in the specification and the appended claims, the singular forms "a", "an," and "the" also include plural referents unless the context clearly dictates otherwise. For example, "a compound" means 1 compound or more than 1 compound.

The terms described above and others used in the specification are well understood to those in the art.

Preferred features of the compounds of this invention are now set forth. The present invention concerns novel compounds of Formula (I):

(I)

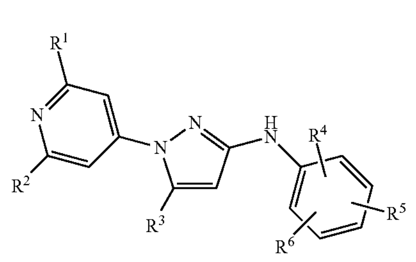

and stereoisomeric forms thereof, wherein $R^1$ and $R^2$ each independently represent hydrogen or $C_{1-4}$alkyl;

$R^3$ is $C_{1-6}$alkyl optionally substituted with one or more substituents independently selected from the group consisting of hydroxyl, cyano, $C_{1-6}$alkyloxy, benzyloxy, $R^xR^yN$—C(═O)—, and $R^zO$—C(═O)—;

$R^x$ and $R^y$ each independently represent hydrogen, $C_{1-4}$alkyl, cyclo$C_{3-6}$alkyl or (cyclo$C_{3-6}$alkyl)$C_{1-4}$alkyl;

$R^z$ represents hydrogen or $C_{1-3}$alkyl;

$R^4$, $R^5$ and $R^6$ each independently represent hydrogen, halo, $C_{1-6}$alkyl, cyano, trifluoromethyl, trifluoromethoxy, or methoxy; or $R^4$ and $R^5$ when attached to 2 vicinal carbon atoms together form a bivalent radical of formula —O—$CF_2$—O—;

and the pharmaceutically acceptable addition salts, and the hydrates and the solvates thereof.

In an embodiment, the present invention relates to those compounds of Formula (I) and stereoisomeric forms thereof, wherein $R^1$ and $R^2$ each independently represent hydrogen or $C_{1-4}$alkyl;

$R^3$ is $C_{1-6}$alkyl optionally substituted with one or more substituents independently selected from the group consisting of hydroxyl, cyano, $C_{1-6}$alkyloxy, benzyloxy, $R^xR^yN$—C(═O)—, and $R^zO$—C(═O)—;

$R^x$ and $R^y$ each independently represent hydrogen, $C_{1-4}$alkyl, cyclo$C_{3-6}$alkyl or (cyclo$C_{3-6}$alkyl)$C_{1-4}$alkyl;

$R^z$ represents hydrogen or $C_{1-3}$alkyl;

$R^4$, $R^5$ and $R^6$ each independently represent halo, $C_{1-6}$alkyl, cyano, trifluoromethyl, trifluoromethoxy, or methoxy; or $R^4$ and $R^5$ when attached to 2 vicinal carbon atoms together form a bivalent radical of formula —O—$CF_2$—O—;

and the pharmaceutically acceptable addition salts, and the hydrates and the solvates thereof.

An embodiment of the present invention relates to those compounds of Formula (I) and stereoisomeric forms thereof, wherein one or more, preferably all, of the following restrictions apply:

(i) $R^1$ and $R^2$ each independently represent hydrogen or methyl;

(ii) $R^3$ is $C_{1-4}$alkyl optionally substituted with one or more substituents independently selected from the group consisting of hydroxyl, cyano, methoxy, benzyloxy, $R^xR^yN$—C(═O)—, and $R^zO$—C(═O)—;

(iii) $R^x$ and $R^y$ each independently represent hydrogen, $C_{1-4}$alkyl, cyclo$C_{3-6}$alkyl or (cyclo$C_{3-6}$alkyl)$C_{1-4}$alkyl;

(iv) $R^z$ represents hydrogen or $C_{1-3}$alkyl;

(v) $R^4$, $R^5$ and $R^6$ each independently represent hydrogen, halo, cyano, trifluoromethyl, trifluoromethoxy, or methoxy; in particular halo, cyano, trifluoromethyl, trifluoromethoxy, or methoxy; or $R^4$ and $R^5$ when attached to 2 vicinal carbon atoms together form a bivalent radical of formula —O—$CF_2$—O—;

and the pharmaceutically acceptable addition salts, and the hydrates and the solvates thereof.

An embodiment of the present invention relates to those compounds of Formula (I) and stereoisomeric forms thereof, wherein (i) $R^1$ and $R^2$ each independently represent hydrogen or methyl;

(ii) $R^3$ is $C_{1-4}$alkyl optionally substituted with one or more substituents independently selected from the group consisting of hydroxyl, cyano, methoxy, benzyloxy, and $R^xR^yN$—C(═O)—;

(iii) $R^x$ and $R^y$ each independently represent hydrogen, $C_{1-4}$alkyl, cyclo$C_{3-6}$alkyl or (cyclo$C_{3-6}$alkyl)$C_{1-4}$alkyl;

(iv) $R^4$, $R^5$ and $R^6$ each independently represent hydrogen, halo, cyano, trifluoromethyl, trifluoromethoxy, or methoxy; in particular halo, cyano, trifluoromethyl, trifluoromethoxy, or methoxy; or $R^4$ and $R^5$ when attached to 2 vicinal carbon atoms together form a bivalent radical of formula —O—$CF_2$—O—;

and the pharmaceutically acceptable addition salts, and the hydrates and the solvates thereof.

Another embodiment of the present invention relates to those compounds of Formula (I), or any subgroup thereof as mentioned in any of the other embodiments wherein one or more, preferably all, of the following restrictions apply:

(i) $R^1$ and $R^2$ each independently represent hydrogen or methyl;

(ii) $R^3$ is $C_{1-4}$alkyl optionally substituted with one or more substituents independently selected from the group consisting of hydroxyl, cyano, methoxy, benzyloxy, $R^xR^yN$—C(═O)—, and $R^zO$—C(═O)—;

(iii) $R^x$ represents hydrogen, methyl, ethyl, cyclopropylmethyl, cyclopropyl, cyclobutyl, or 1-methylethyl;

(iv) $R^y$ represents hydrogen or methyl;

(v) $R^z$ represents hydrogen or methyl;

(vi) $R^4$, $R^5$ and $R^6$ each independently represent hydrogen, halo, cyano, trifluoromethyl, trifluoromethoxy, or methoxy; in particular halo, cyano, trifluoromethyl, trifluoromethoxy, or methoxy; or $R^4$ and $R^5$ when attached to 2 vicinal carbon atoms together form a bivalent radical of formula —O—$CF_2$—O—;

and the pharmaceutically acceptable addition salts, and the hydrates and the solvates thereof.

Another embodiment of the present invention relates to those compounds of Formula (I), or any subgroup thereof as mentioned in any of the other embodiments wherein one or more, preferably all, of the following restrictions apply:

(i) $R^1$ and $R^2$ each independently represent hydrogen or methyl;

(ii) $R^3$ is methyl; hydroxymethyl; hydroxypropyl; (2R)-2-hydroxybutyl; (2S)-2-hydroxybutyl; methoxymethyl; cyanomethyl; carboxymethyl; carboxyethyl; 2-methoxy-2-oxoethyl; 3-methoxy-3-oxopropyl; 2-methylamino-2-oxoethyl; 2-ethylamino-2-oxoethyl; 2-[(cyclopropylmethyl)amino]-2-oxoethyl; 2-(cyclopropylamino)-2-oxoethyl; 2-(cyclobutylamino)-2-oxoethyl; 3-(dimethylamino)-3-oxopropyl; benzyloxymethyl; benzyloxypropyl; or 2-[(1-methylethyl)amino]-2-oxoethyl;

(iii) $R^4$, $R^5$ and $R^6$ each independently represent hydrogen, chloro, fluoro, bromo, cyano, trifluoromethyl, trifluoromethoxy, or methoxy; in particular chloro, fluoro, bromo, cyano, trifluoromethyl, trifluoromethoxy, or methoxy; or $R^4$ and $R^5$ when attached to 2 vicinal carbon atoms together form a bivalent radical of formula —O—$CF_2$—O—;

and the pharmaceutically acceptable addition salts, and the hydrates and the solvates thereof.

Another embodiment of the present invention relates to those compounds of Formula (I), or any subgroup thereof as mentioned in any of the other embodiments wherein the following restrictions applies:

$R^3$ is methyl; hydroxymethyl; hydroxypropyl; (2R)-2-hydroxybutyl; (2S)-2-hydroxybutyl; (2R)-2-hydroxypropyl; (2S)-2-hydroxypropyl; methoxymethyl; cyanomethyl; carboxymethyl; carboxyethyl; 2-methoxy-2-oxoethyl; 3-methoxy-3-oxopropyl; 2-methylamino-2-oxoethyl; 2-ethylamino-2-oxoethyl; 2-[(cyclopropylmethyl)amino]-2-oxoethyl; 2-(cyclopropylamino)-2-oxoethyl; 2-(cyclobutylamino)-2-oxoethyl; 3-(dimethylamino)-3-oxopropyl; benzyloxymethyl; benzyloxypropyl; or 2-[(1-methylethyl)amino]-2-oxoethyl;

and the pharmaceutically acceptable addition salts, and the hydrates and the solvates thereof.

An embodiment of the present invention relates to those compounds of formula (I) or any subgroup thereof as mentioned in any of the other embodiments wherein one or more of the following restrictions apply:

(i) $R^3$ is $C_{1-6}$alkyl optionally substituted with one or more substituents independently selected from the group consisting of hydroxyl, cyano, methoxy, benzyloxy, and $R^xR^yN—C(=O)—$;

(ii) $R^4$, $R^5$ and $R^6$ each independently represent hydrogen, halo, $C_{1-6}$alkyl, cyano, trifluoromethyl, trifluoromethoxy, or methoxy; in particular halo, $C_{1-6}$alkyl, cyano, trifluoromethyl, trifluoromethoxy, or methoxy.

An embodiment of the present invention relates to those compounds of formula (I) or any subgroup thereof as mentioned in any of the other embodiments wherein one or more of the following restrictions apply:

(i) $R^3$ is $C_{1-4}$alkyl optionally substituted with one or more substituents independently selected from the group consisting of hydroxyl, cyano, methoxy, benzyloxy, and $R^xR^yN—C(=O)—$;

(ii) $R^4$, $R^5$ and $R^6$ each independently represent hydrogen, halo, cyano, trifluoromethyl, trifluoromethoxy, or methoxy; in particular halo, cyano, trifluoromethyl, trifluoromethoxy, or methoxy.

An embodiment of the present invention relates to those compounds of formula (I) or any subgroup thereof as mentioned in any of the other embodiments wherein the following restriction applies: $R^6$ represents hydrogen, halo, cyano, trifluoromethyl, $C_{1-6}$alkyl, trifluoromethoxy, or methoxy; in particular halo, cyano, trifluoromethyl, $C_{1-6}$alkyl, trifluoromethoxy, or methoxy; and $R^4$ and $R^5$ are attached to 2 vicinal carbon atoms and form together a bivalent radical of formula $—O—CF_2—O—$.

An embodiment of the present invention relates to those compounds of formula (I) or any subgroup thereof as mentioned in any of the other embodiments wherein the following restriction applies: $R^6$ represents hydrogen, halo, cyano, trifluoromethyl, trifluoromethoxy, or methoxy; in particular halo, cyano, trifluoromethyl, trifluoromethoxy, or methoxy; and $R^4$ and $R^5$ are attached to 2 vicinal carbon atoms and form together a bivalent radical of formula $—O—CF_2—O—$.

An embodiment of the present invention relates to those compounds of formula (I) or any subgroup thereof as mentioned in any of the other embodiments wherein one or more of the following restrictions apply:

(i) $R^3$ is $C_{1-6}$alkyl, in particular $C_{1-4}$alkyl, optionally substituted with one or more substituents independently selected from the group consisting of hydroxyl, and $R^xR^yN—C(=O)—$;

(ii) $R^x$ and $R^y$ each independently represent hydrogen, $C_{1-4}$alkyl, cyclo$C_{3-6}$alkyl or (cyclo$C_{3-6}$alkyl)$C_{1-4}$alkyl;

(iii) $R^4$, $R^5$ and $R^6$ each independently represent hydrogen, halo, trifluoromethyl, trifluoromethoxy, or methoxy; in particular halo, trifluoromethyl, trifluoromethoxy, or methoxy; or $R^4$ and $R^5$ when attached to 2 vicinal carbon atoms together form a bivalent radical of formula $—O—CF_2—O—$;

and the pharmaceutically acceptable addition salts, and the hydrates and the solvates thereof.

An embodiment of the present invention relates to those compounds of formula (I) or any subgroup thereof as mentioned in any of the other embodiments wherein at least one of $R^4$, $R^5$ or $R^6$ is other than hydrogen.

An embodiment of the present invention relates to those compounds of formula (I) or any subgroup thereof as mentioned in any of the other embodiments wherein $R^4$, $R^5$ and $R^6$ each independently represent hydrogen, halo, $C_{1-6}$alkyl, cyano, trifluoromethyl, trifluoromethoxy, or methoxy; in particular halo, $C_{1-6}$alkyl, cyano, trifluoromethyl, trifluoromethoxy, or methoxy.

An embodiment of the present invention relates to those compounds of formula (I) or any subgroup thereof as mentioned in any of the other embodiments wherein $R^4$ and $R^5$ are attached to 2 vicinal carbon atoms and together form a bivalent radical of formula $—O—CF_2—O—$; and $R^6$ is hydrogen.

In an embodiment the compound of Formula (I) is selected from the group comprising:

N-(3,4-difluorophenyl)-5-methyl-1-(2-methyl-4-pyridinyl)-1H-pyrazol-3-amine,

N-(3,4-difluorophenyl)-1-(2-methyl-4-pyridinyl)-5-[(phenylmethoxy)methyl]-1H-pyrazol-3-amine, 3-[(3,4-difluorophenyl)amino]-1-(2-methyl-4-pyridinyl)-1H-pyrazole-5-methanol, (alphaR)-3-[(3,4-difluorophenyl)amino]-alpha-ethyl-1-(2-methyl-4-pyridinyl)-1H-pyrazole-5-ethanol, (alphaR)-alpha-ethyl-1-(2-methyl-4-pyridinyl)-3-[[3-(trifluoromethyl)phenyl]amino]-1H-pyrazole-5-ethanol, N-(3,4-difluorophenyl)-5-(methoxymethyl)-1-(2-methyl-4-pyridinyl)-1H-pyrazol-3-amine, 3-[(3,4-difluorophenyl)amino]-1-(2-methyl-4-pyridinyl)-1H-pyrazole-5-acetonitrile, (alphaS)-alpha-ethyl-1-(2-methyl-4-pyridinyl)-3-[[3-(trifluoromethyl)phenyl]amino]-1H-pyrazole-5-ethanol, 3-[(3,4-difluorophenyl)amino]-1-(2-methyl-4-pyridinyl)-1H-pyrazole-5-acetic acid methyl ester.HCl 3-[(3,4-difluorophenyl)amino]-N-methyl-1-(2-methyl-4-pyridinyl)-1H-pyrazole-5-acetamide, 3-[(3,4-difluorophenyl)amino]-1-(2-methyl-4-pyridinyl)-1H-pyrazole-5-acetic acid, (alphaS)-3-[(3,4-difluorophenyl)amino]-alpha-ethyl-1-(2-methyl-4-pyridinyl)-1H-pyrazole-5-ethanol, 3-[(3,4-difluorophenyl)amino]-N-ethyl-1-(2-methyl-4-pyridinyl)-1H-pyrazole-5-acetamide, N-(cyclopropylmethyl)-3-[(3,4-difluorophenyl)amino]-1-(2-methyl-4-pyridinyl)-1H-pyrazole-5-acetamide, N-(3,4-difluorophenyl)-1-(2-methyl-4-pyridinyl)-5-[3-(phenylmethoxy)propyl]-1H-pyrazol-3-amine, (alphaS)-3-[(2,2-difluoro-1,3-benzodioxol-5-yl)amino]-alpha-ethyl-1-(2-methyl-4-pyridinyl)-1H-pyrazole-5-ethanol, (alphaS)-alpha-ethyl-3-[[3-methoxy-5-(trifluoromethyl)phenyl]amino]-1-(2-methyl-4-pyridinyl)-1H-pyrazole-5-ethanol, (alphaS)-alpha-ethyl-1-(2-methyl-4-pyridinyl)-3-[(2,3,4-trifluorophenyl)amino]-1H-pyrazole-5-ethanol, (alphaS)-alpha-ethyl-1-(2-methyl-4-pyridinyl)-3-[[3-(trifluoromethoxy)phenyl]amino]-1H-pyrazole-5-ethanol, (alphaS)-alpha-ethyl-3-[[4-methoxy-3-(trifluoromethyl)phenyl]amino]-1-(2-methyl-4-pyridinyl)-1H-pyrazole-5-ethanol, (alphaS)-3-[(3-chlorophenyl)amino]-alpha-ethyl-1-(2-methyl-4-pyridinyl)-1H-pyrazole-5-ethanol, (alphaS)-3-[(3-chloro-5-methoxyphenyl)amino]-alpha-ethyl-1-(2-methyl-4-pyridinyl)-1H-pyrazole-5-ethanol, 5-bromo-2-[[5-[(2S)-2-hydroxybutyl]-1-(2-methyl-4-pyridinyl)-1H-pyrazol-3-yl]amino]-benzonitrile, (alphaS)-alpha-ethyl-1-(2-methyl-4-pyridinyl)-3-[(2,4,5-trifluorophenyl)amino]-1H-pyrazole-5-ethanol, (alphaS)-3-[(3-chloro-2-fluorophenyl)amino]-alpha-ethyl-1-(2-methyl-4-pyridinyl)-1H-pyrazole-5-ethanol, N-(2,2-difluoro-1,3-benzodioxol-5-yl)-1-(2-methyl-4-pyridinyl)-5-[3-(phenylmethoxy)propyl]-1H-pyrazol-3-amine, 3-[(3,4-difluorophenyl)amino]-1-(2-methyl-4-pyridinyl)-1H-pyrazole-5-propanol, 3-[(3,4-difluorophenyl)amino]-1-(2-methyl-4-pyridinyl)-1H-pyrazole-5-propanoic acid, N-(3-chloro-2-fluorophenyl)-1-(2-methyl-4-pyridinyl)-5-[(phenylmethoxy)methyl]-1H-pyrazol-3-amine,
3-[(3-chloro-2-fluorophenyl)amino]-1-(2-methyl-4-pyridinyl)-1H-pyrazole-5-methanol,
3-[(3-chloro-2-fluorophenyl)amino]-1-(2-methyl-4-pyridinyl)-1H-pyrazole-5-acetonitrile,
3-[(3,4-difluorophenyl)amino]-N,N-dimethyl-1-(2-methyl-4-pyridinyl)-1H-pyrazole-5-propanamide,
N,N-dimethyl-1-(2-methyl-4-pyridinyl)-3-[[3-(trifluoromethyl)phenyl]amino]-1H-pyrazole-5-propanamide,
3-[[3-methoxy-5-(trifluoromethyl)phenyl]amino]-1-(2-methyl-4-pyridinyl)-1H-pyrazole-5-propanol,
3-[(3-chloro-2-fluorophenyl)amino]-1-(2-methyl-4-pyridinyl)-1H-pyrazole-5-acetic acid methyl ester,
1-(2-methyl-4-pyridinyl)-5-[3-(phenylmethoxy)propyl]-N-[3-(trifluoromethyl)phenyl]-1H-pyrazol-3-amine,
N-[3-methoxy-5-(trifluoromethyl)phenyl]-1-(2-methyl-4-pyridinyl)-5-[3-(phenylmethoxy)propyl]-1H-pyrazol-3-amine,
3-[(3-chloro-2-fluorophenyl)amino]-N-methyl-1-(2-methyl-4-pyridinyl)-1H-pyrazole-5-acetamide,
3-[(3-chloro-2-fluorophenyl)amino]-N-ethyl-1-(2-methyl-4-pyridinyl)-1H-pyrazole-5-acetamide,
3-[(2,2-difluoro-1,3-benzodioxol-5-yl)amino]-1-(2-methyl-4-pyridinyl)-1H-pyrazole-5-propanol,
3-[(3-chloro-2-fluorophenyl)amino]-N-(cyclopropylmethyl)-1-(2-methyl-4-pyridinyl)-1H-pyrazole-5-acetamide,
N-(2,2-difluoro-1,3-benzodioxol-5-yl)-1-(2-methyl-4-pyridinyl)-5-[(phenylmethoxy)methyl]-1H-pyrazol-3-amine,
1-(2-methyl-4-pyridinyl)-3-[[3-(trifluoromethyl)phenyl]amino]-1H-pyrazole-5-acetonitrile,
1-(2-methyl-4-pyridinyl)-5-[(phenylmethoxy)methyl]-N-[3-(trifluoromethyl)phenyl]-1H-pyrazol-3-amine,
1-(2-methyl-4-pyridinyl)-3-[[3-(trifluoromethyl)phenyl]amino]-1H-pyrazole-5-methanol,
3-[[3-methoxy-5-(trifluoromethyl)phenyl]amino]-N,N-dimethyl-1-(2-methyl-4-pyridinyl)-1H-pyrazole-5-propanamide,
3-[(3-chloro-2-fluorophenyl)amino]-N,N-dimethyl-1-(2-methyl-4-pyridinyl)-1H-pyrazole-5-propanamide,
3-[[3-methoxy-5-(trifluoromethyl)phenyl]amino]-1-(2-methyl-4-pyridinyl)-1H-pyrazole-5-propanoic acid,
1-(2-methyl-4-pyridinyl)-3-[[3-(trifluoromethyl)phenyl]amino]-1H-pyrazole-5-acetic acid methyl ester,
N-methyl-1-(2-methyl-4-pyridinyl)-3-[[3-(trifluoromethyl)phenyl]amino]-1H-pyrazole-5-acetamide,
N-ethyl-1-(2-methyl-4-pyridinyl)-3-[[3-(trifluoromethyl)phenyl]amino]-1H-pyrazole-5-acetamide,
N-(cyclopropylmethyl)-1-(2-methyl-4-pyridinyl)-3-[[3-(trifluoromethyl)phenyl]amino]-1H-pyrazole-5-acetamide,
N-[3-methoxy-5-(trifluoromethyl)phenyl]-1-(2-methyl-4-pyridinyl)-5-[(phenylmethoxy)methyl]-1H-pyrazol-3-amine,
3-[(2,2-difluoro-1,3-benzodioxol-5-yl)amino]-N,N-dimethyl-1-(2-methyl-4-pyridinyl)-1H-pyrazole-5-propanamide,
3-[(3-chloro-2-fluorophenyl)amino]-N-cyclopropyl-1-(2-methyl-4-pyridinyl)-1H-pyrazole-5-acetamide,
3-[(3-chloro-2-fluorophenyl)amino]-N-cyclobutyl-1-(2-methyl-4-pyridinyl)-1H-pyrazole-5-acetamide,
3-[(2,2-difluoro-1,3-benzodioxol-5-yl)amino]-1-(2-methyl-4-pyridinyl)-1H-pyrazole-5-propanoic acid,
3-[(2,2-difluoro-1,3-benzodioxol-5-yl)amino]-1-(2-methyl-4-pyridinyl)-1H-pyrazole-5-methanol, 3-[(2,2-difluoro-1,3-benzodioxol-5-yl)amino]-1-(2-methyl-4-pyridinyl)-1H-pyrazole-5-acetonitrile,
3-[(2,2-difluoro-1,3-benzodioxol-5-yl)amino]-1-(2-methyl-4-pyridinyl)-1H-pyrazole-5-acetic acid methyl ester,
N-(cyclopropylmethyl)-3-[(2,2-difluoro-1,3-benzodioxol-5-yl)amino]-1-(2-methyl-4-pyridinyl)-1H-pyrazole-5-acetamide,
1-(2-methyl-4-pyridinyl)-3-[[3-(trifluoromethyl)phenyl]amino]-1H-pyrazole-5-propanol,
1-(2-methyl-4-pyridinyl)-3-[[3-(trifluoromethyl)phenyl]amino]-1H-pyrazole-5-propanoic acid methyl ester,
1-(2-methyl-4-pyridinyl)-3-[[3-(trifluoromethyl)phenyl]amino]-1H-pyrazole-5-propanoic acid,
3-[[3-methoxy-5-(trifluoromethyl)phenyl]amino]-1-(2-methyl-4-pyridinyl)-1H-pyrazole-5-methanol,
3-[[3-methoxy-5-(trifluoromethyl)phenyl]amino]-1-(2-methyl-4-pyridinyl)-1H-pyrazole-5-acetonitrile,
3-[(2,2-difluoro-1,3-benzodioxol-5-yl)amino]-N-ethyl-1-(2-methyl-4-pyridinyl)-1H-pyrazole-5-acetamide,
3-[(3-chloro-5-methoxyphenyl)amino]-N,N-dimethyl-1-(2-methyl-4-pyridinyl)-1H-pyrazole-5-propanamide,
3-[[3-methoxy-5-(trifluoromethyl)phenyl]amino]-1-(2-methyl-4-pyridinyl)-1H-pyrazole-5-acetic acid methyl ester,
3-[[3-methoxy-5-(trifluoromethyl)phenyl]amino]-N-methyl-1-(2-methyl-4-pyridinyl)-1H-pyrazole-5-acetamide,
N-(3-chloro-2-fluorophenyl)-1-(2-methyl-4-pyridinyl)-5-[3-(phenylmethoxy)propyl]-1H-pyrazol-3-amine,
3-[(3-chloro-2-fluorophenyl)amino]-1-(2-methyl-4-pyridinyl)-1H-pyrazole-5-propanol,
3-[(3-chloro-2-fluorophenyl)amino]-1-(2-methyl-4-pyridinyl)-1H-pyrazole-5-propanoic acid,
N-(3-chloro-5-methoxyphenyl)-1-(2-methyl-4-pyridinyl)-5-[(phenylmethoxy)methyl]-1H-pyrazol-3-amine,
3-[(3-chloro-5-methoxyphenyl)amino]-1-(2-methyl-4-pyridinyl)-1H-pyrazole-5-methanol,
3-[(3-chloro-5-methoxyphenyl)amino]-1-(2-methyl-4-pyridinyl)-1H-pyrazole-5-acetonitrile,
3-[(3-chloro-5-methoxyphenyl)amino]-1-(2-methyl-4-pyridinyl)-1H-pyrazole-5-acetic acid methyl ester,
N-ethyl-3-[[3-methoxy-5-(trifluoromethyl)phenyl]amino]-1-(2-methyl-4-pyridinyl)-1H-pyrazole-5-acetamide,
3-[(3-chloro-5-methoxyphenyl)amino]-N-methyl-1-(2-methyl-4-pyridinyl)-1H-pyrazole-5-acetamide,
3-[(3-chloro-5-methoxyphenyl)amino]-N-ethyl-1-(2-methyl-4-pyridinyl)-1H-pyrazole-5-acetamide,
3-[(3-chloro-5-methoxyphenyl)amino]-N-(cyclopropylmethyl)-1-(2-methyl-4-pyridinyl)-1H-pyrazole-5-acetamide,
3-[(3-chloro-5-methoxyphenyl)amino]-N-cyclopropyl-1-(2-methyl-4-pyridinyl)-1H-pyrazole-5-acetamide,
3-[(3-chloro-5-methoxyphenyl)amino]-N-cyclobutyl-1-(2-methyl-4-pyridinyl)-1H-pyrazole-5-acetamide,
N-(cyclopropylmethyl)-3-[[3-methoxy-5-(trifluoromethyl)phenyl]amino]-1-(2-methyl-4-pyridinyl)-1H-pyrazole-5-acetamide,
N-cyclobutyl-3-[[3-methoxy-5-(trifluoromethyl)phenyl]amino]-1-(2-methyl-4-pyridinyl)-1H-pyrazole-5-acetamide,
1-(2-methyl-4-pyridinyl)-5-[(phenylmethoxy)methyl]-N-[3-(trifluoromethoxy)phenyl]-1H-pyrazol-3-amine,
N-cyclopropyl-3-[[3-methoxy-5-(trifluoromethyl)phenyl]amino]-1-(2-methyl-4-pyridinyl)-1H-pyrazole-5-acetamide,
N-(3-chloro-5-methoxyphenyl)-1-(2-methyl-4-pyridinyl)-5-[3-(phenylmethoxy)propyl]-1H-pyrazol-3-amine,
3-[(3-chloro-5-methoxyphenyl)amino]-1-(2-methyl-4-pyridinyl)-1H-pyrazole-5-propanol, 3-[(3-chloro-5-methoxyphenyl)amino]-1-(2-methyl-4-pyridinyl)-1H-pyrazole-5-propanoic acid, N-cyclopropyl-3-[(2,2-difluoro-1,3-benzodioxol-5-yl)amino]-1-(2-methyl-4-pyridinyl)-1H-pyrazole-5-acetamide, N-cyclobutyl-3-[(2,2-difluoro-1,3-benzodioxol-5-yl)amino]-1-(2-methyl-4-pyridinyl)-1H-pyrazole-5-acetamide, 3-[(2,2-difluoro-1,3-benzodioxol-5-yl)amino]-N-methyl-1-(2-methyl-4-pyridinyl)-1H-pyrazole-5-acetamide, 1-(2-methyl-4-pyridinyl)-3-[[3-(trifluoromethoxy)phenyl]amino]-1H-pyrazole-5-acetonitrile, 1-(2-methyl-4-pyridinyl)-3-[[3-(trifluoromethoxy)phenyl]amino]-1H-pyrazole-5-acetic acid methyl ester, 1-(2-methyl-4-pyridinyl)-3-[[3-(trifluoromethoxy)phenyl]amino]-1H-pyrazole-5-methanol, N-methyl-1-(2-methyl-4-pyridinyl)-3-[[3-(trifluoromethoxy)phenyl]amino]-1H-pyrazole-5-acetamide, N-(cyclopropylmethyl)-1-(2-methyl-4-pyridinyl)-3-[[3-(trifluoromethoxy)phenyl]amino]-1H-pyrazole-5-acetamide, N-cyclopropyl-1-(2-methyl-4-pyridinyl)-3-[[3-(trifluoromethoxy)phenyl]amino]-1H-pyrazole-5-acetamide, N-ethyl-1-(2-methyl-4-pyridinyl)-3-[[3-(trifluoromethoxy)phenyl]amino]-1H-pyrazole-5-acetamide, N-cyclobutyl-1-(2-methyl-4-pyridinyl)-3-[[3-(trifluoromethoxy)phenyl]amino]-1H-pyrazole-5-acetamide, N-(3-chloro-2-fluorophenyl)-1-(2,6-dimethyl-4-pyridinyl)-5-[(phenylmethoxy)methyl]-1H-pyrazol-3-amine, 3-[(3-chloro-2-fluorophenyl)amino]-1-(2,6-dimethyl-4-pyridinyl)-1H-pyrazole-5-methanol, 3-[(3-chloro-2-fluorophenyl)amino]-1-(2,6-dimethyl-4-pyridinyl)-1H-pyrazole-5-acetonitrile, 3-[(3-chloro-2-fluorophenyl)amino]-1-(2,6-dimethyl-4-pyridinyl)-1H-pyrazole-5-acetic acid methyl ester 3-[(3-chloro-2-fluorophenyl)amino]-N-(cyclopropylmethyl)-1-(2,6-dimethyl-4-pyridinyl)-1H-pyrazole-5-acetamide, 3-[(3-chloro-2-fluorophenyl)amino]-1-(2,6-dimethyl-4-pyridinyl)-N-ethyl-1H-pyrazole-5-acetamide, 3-[(3-chloro-2-fluorophenyl)amino]-N-cyclopropyl-1-(2,6-dimethyl-4-pyridinyl)-1H-pyrazole-5-acetamide, N-(1-methylethyl)-1-(2-methyl-4-pyridinyl)-3-[[3-(trifluoromethoxy)phenyl]amino]-1H-pyrazole-5-acetamide, 1-(2,6-dimethyl-4-pyridinyl)-5-[(phenylmethoxy)methyl]-N-[3-(trifluoromethoxy)phenyl]-1H-pyrazol-3-amine, 1-(2,6-dimethyl-4-pyridinyl)-3-[[3-(trifluoromethoxy)phenyl]amino]-1H-pyrazole-5-acetonitrile, 1-(2,6-dimethyl-4-pyridinyl)-3-[[3-(trifluoromethoxy)phenyl]amino]-1H-pyrazole-5-acetic acid methyl ester, 1-(2,6-dimethyl-4-pyridinyl)-N-methyl-3-[[3-(trifluoromethoxy)phenyl]amino]-1H-pyrazole-5-acetamide, 1-(2,6-dimethyl-4-pyridinyl)-N-ethyl-3-[[3-(trifluoromethoxy)phenyl]amino]-1H-pyrazole-5-acetamide, N-(cyclopropylmethyl)-1-(2,6-dimethyl-4-pyridinyl)-3-[[3-(trifluoromethoxy)phenyl]amino]-1H-pyrazole-5-acetamide, N-cyclopropyl-1-(2,6-dimethyl-4-pyridinyl)-3-[[3-(trifluoromethoxy)phenyl]amino]-1H-pyrazole-5-acetamide, 1-(2,6-dimethyl-4-pyridinyl)-N-(1-methylethyl)-3-[[3-(trifluoromethoxy)phenyl]amino]-1H-pyrazole-5-acetamide, (alphaS)-alpha-ethyl-1-(2-methyl-4-pyridinyl)-3-[(3,4,5-trifluorophenyl)amino]-1H-pyrazole-5-ethanol, (alphaR)-alpha-ethyl-1-(2-methyl-4-pyridinyl)-3-[(3,4,5-trifluorophenyl)amino]-1H-pyrazole-5-ethanol, (alphaR)-3-[(3-chloro-2-fluorophenyl)amino]-alpha-ethyl-1-(2-methyl-4-pyridinyl)-1H-pyrazole-5-ethanol, (alphaR)-alpha-ethyl-1-(2-methyl-4-pyridinyl)-3-[(2,3,4-trifluorophenyl)amino]-1H-pyrazole-5-ethanol, (alphaR)-alpha-ethyl-3-[[3-methoxy-5-(trifluoromethyl)phenyl]amino]-1-(2-methyl-4-pyridinyl)-1H-pyrazole-5-ethanol, (alphaR)-3-[(3-chloro-5-methoxyphenyl)amino]-alpha-ethyl-1-(2-methyl-4-pyridinyl)-1H-pyrazole-5-ethanol, (alphaR)-3-[(3-chloro-5-fluorophenyl)amino]-alpha-ethyl-1-(2-methyl-4-pyridinyl)-1H-pyrazole-5-ethanol, including any stereochemically isomeric form thereof, and the pharmaceutically acceptable addition salts and the solvates thereof.

Preparation of the Compounds

A compound according to the invention can generally be prepared by a succession of steps, each of which is known to the skilled person. In particular, the compounds in this patent application can be prepared according to one or more of the following preparation methods. In the following schemes, and unless otherwise indicated, all variables are used as defined in Formula (I).

Scheme 1

Reaction Scheme 1

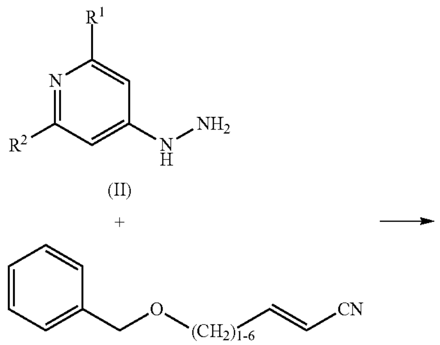
(II)

-continued

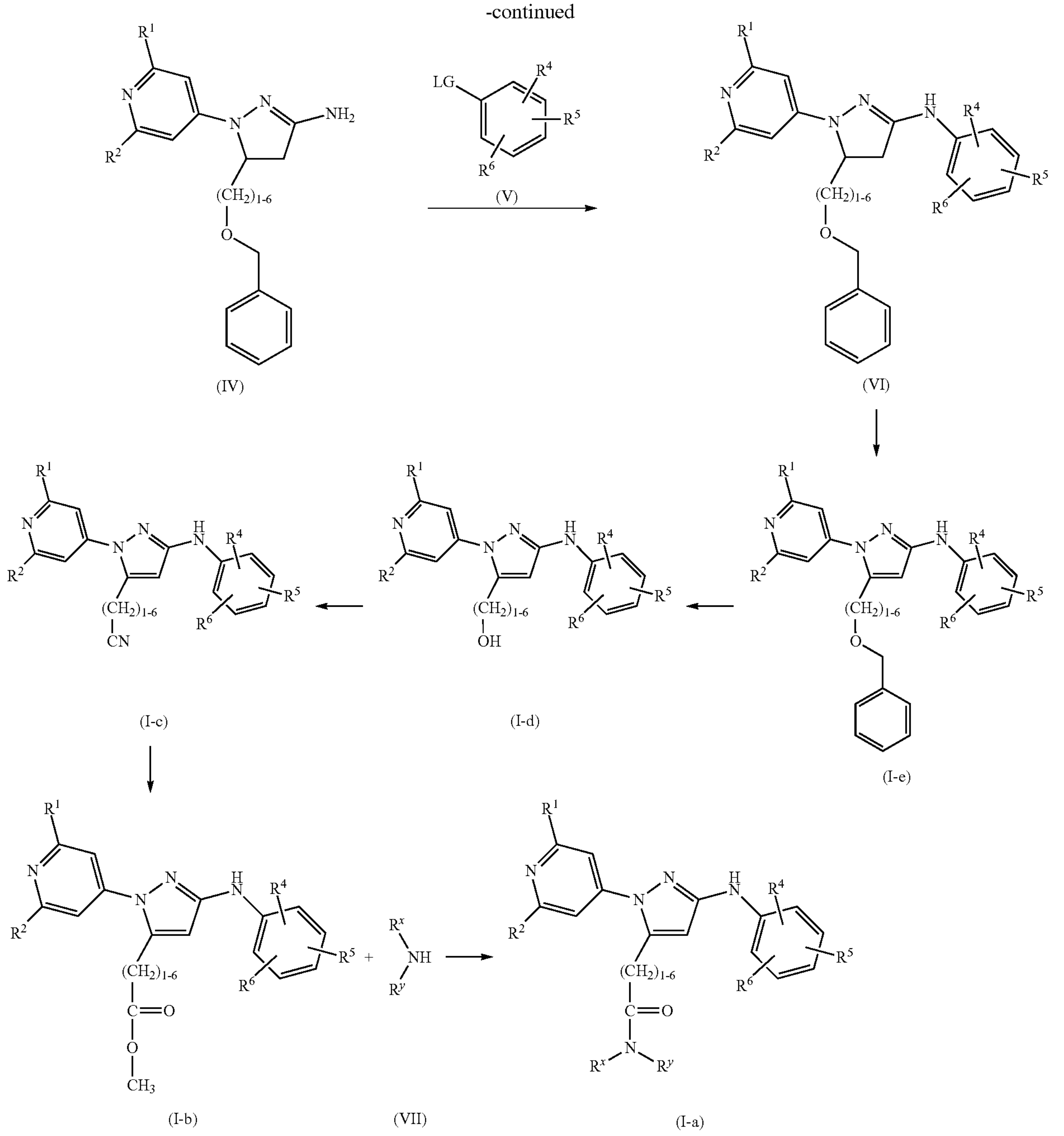

(IV) (V) (VI) (I-e) (I-d) (I-c) (I-b) (VII) (I-a)

Compounds of this invention according to formula (I-a), (I-b), (I-c), (I-d), and (I-e) can be prepared by any of several standard synthetic processes commonly used by those skilled in the art of organic chemistry.

In a first step, intermediates of formula (IV) are generally prepared by a ring closure reaction between an intermediate of formula (II) and an intermediate of formula (III) under art known conditions. This transformation is typically performed in a protic solvent, in particular an alcohol such as, for example, ethanol (EtOH) in the presence of a strong base such as, for example, sodium ethoxide or metallic sodium. Stirring and elevated temperatures may enhance the rate of the reaction. Intermediates of formula (II) and (III) are commercially available or can be easily prepared by those skilled in the art.

In a second step, intermediates of formula (VI) can be prepared in a coupling reaction between an amino derivative of formula (IV) and an intermediate of formula (V) using transition metal catalysis. LG is defined as a leaving group such as, for example, Cl, Br, I, tosylate, mesylate or triflate, in particular F, Cl, Br or I, more in particular Cl, Br or I, even more in particular Br. Typically a palladium catalyst is used in this type of reaction, for example, $Pd_2(dba)_3$. The palladium catalyzed coupling reaction typically is performed in the presence of a bidentate phosphine ligand such as, for example, [1,1'-binaphthalene]-2,2'-diylbis[diphenylphosphine] (BINAP) or the like and in the presence of a strong inorganic base such as, for example, potassium or sodium tert-butoxide (NaOtBu). This type of reaction can be successfully carried out in an aprotic solvent such as, for example tetrahydrofuran (THF) or the like, at elevated temperatures, in particular between 100° C. and 130° C. Intermediates of formula (V) are commercially available or can be easily prepared by those skilled in the art.

A compound of formula (I-e) can be synthesized by reacting an intermediate of formula (VI) in the presence of an oxidation agent such as, for example, $MnO_2$ in the presence of a suitable solvent such as, for example dichloromethane (DCM).

Compounds of formula (I-e) can be converted into a compound of formula (I-d) by reaction with a suitable de-alkylating agent, such as for example $BBr_3$, in the presence of a suitable solvent, such as for example DCM or dichloroethane (DCE). Alternatively, compounds of formula (I-d) may be prepared by catalytic hydrogenation of compounds of formula (I-e). Pd/C may be used as the catalyst. The reaction is performed in the presence of a hydrogen source such as $H_2$ or hydrazine and in the presence of a solvent such as an alcohol, typically MeOH or EtOH. Stirring and elevated temperatures may enhance the rate of the reaction.

Subsequently, compounds of formula (I-c) can be prepared by treating a compound of formula (I-d) in a first step with a sulfonic acid halide such as, for example, mesyl chloride or tosyl chloride in the presence of an amine base, such as triethyl amine. This reaction may be performed in a suitable solvent such as typically THF. In a second step of the reaction, a cyanide source such as an alkali metal cyanide, typically NaCN, is added together with an organic solvent such as dimethyl sulfoxide (DMSO).

In a next reaction step, compounds of the general formula (I-c) are first subjected to hydrolysis and subsequently to a Fischer esterification to yield a compound of formula (I-b). Usually this type of reaction is performed in an aqueous acid such as, for example an aqueous HCl solution at an elevated temperature such as 70° C. or reflux temperature. Subsequently, the carboxylic acid derivative formed in this reaction undergoes an acid-catalyzed condensation with the desired alcohol (methanol (MeOH), ethanol (EtOH) or the like) in the presence of an acid such as typically HCl.

Finally, compounds of formula (I-b) can be further reacted with amines of formula (VII) to yield a compound of formula (I-a). Dependent on the choice of amine, a suitable solvent can be used for the reaction. A preferred solvent is a protic solvent, such as a lower alkyl alcohol, for instance MeOH or the like. This reaction can be performed by using reaction conditions well-known to those skilled in the art, dependent on the choice of amine.

Scheme 2

Reaction Scheme 2

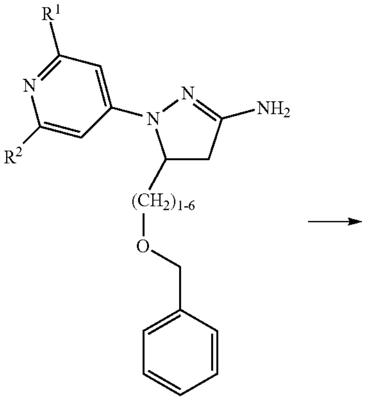

(IV)

-continued

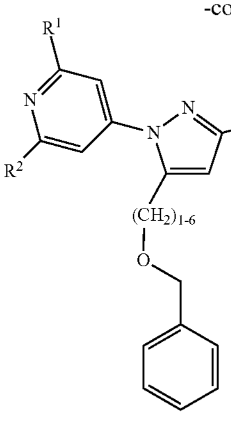

(VIII)

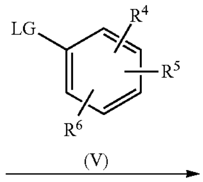

(V)

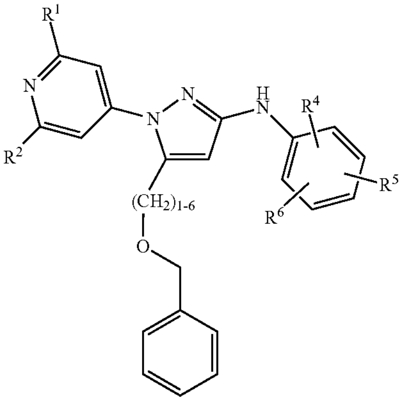

(I-e)

Alternatively, compounds of formula (I-e) can be prepared from intermediates of formula (VIII) according to the reaction protocol described in Scheme 2.

An intermediate of formula (VIII) can be synthesized by reacting an intermediate of formula (IV) in the presence of an oxidation agent such as, for example, $MnO_2$ in the presence of a suitable solvent such as, for example dichloromethane (DCM).

Subsequently, a compound of formula (I-e) can be prepared in a coupling reaction between an amino derivative of formula (VIII) and an intermediate of formula (V) using transition metal catalysis. LG is defined as a leaving group such as, for example, Cl, Br, I, tosylate, mesylate or triflate, in particular F, Cl, Br or I, more in particular Cl, Br or I, even more in particular Br. Typically a palladium catalyst is used in this type of reaction, for example, $Pd_2(dba)_3$. The palladium catalyzed coupling reaction typically is performed in the presence of a bidentate phosphine ligand such as, for example, [1,1'-binaphthalene]-2,2'-diylbis[diphenylphosphine] (BINAP) or the like and in the presence of a strong inorganic base such as, for example, potassium or sodium tert-butoxide (NaOtBu). This type of reaction can be successfully carried out in an aprotic solvent such as, for example tetrahydrofuran (THF) or the like, at elevated temperatures, in particular between 100° C. and 130° C.

Scheme 3

Reaction Scheme 3

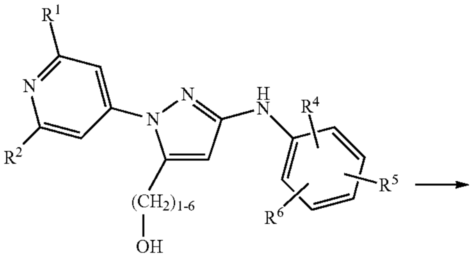

(I-d)

-continued

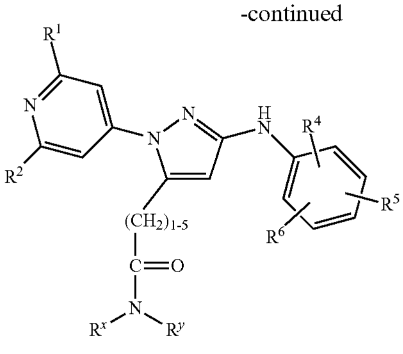

(I-f)

In the first step of Scheme 3, the alcohol of formula (I-d) is converted to a compound of formula (I-g) by using an oxidizing reagent such as, for example, dipyridinium dichromate (PDC) in the presence of a strong acid such as, for example, $H_2SO_4$, in an aprotic solvent, such as DMF or the like.

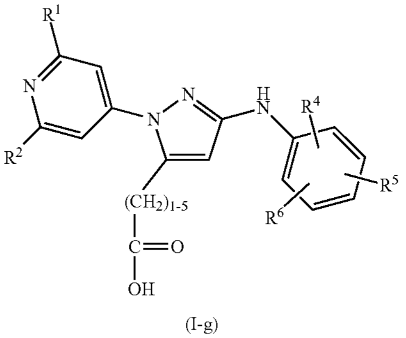

(I-g)

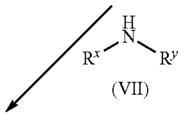

(VII)

Alternatively, compounds of formula (I-g) can also be prepared by following the reaction steps described in Scheme 1. Hydrolysis of the compounds of formula (I-c) yield compounds of the general formula (I-g).

Finally compounds of formula (I-g) are reacted with primary or secondary amines of formula (VII), to yield compounds of formula (I-f). This reaction can be performed by using art known procedures and is typically performed in the presence of a conventional amide coupling reagent such as HBTU (O-benzotriazole-N,N,N',N'-tetramethyl uronium hexafluorophosphate), EDCI, or EDAC in an aprotic solvent like DCM, or more preferably in a polar aprotic solvent like THF or DMF in the presence of an amine base additive, such as diisopropyl ethyl amine (DIPEA). Under certain circumstances the use of HOBT as an additive is an advantage.

Scheme 4

Reaction Scheme 4

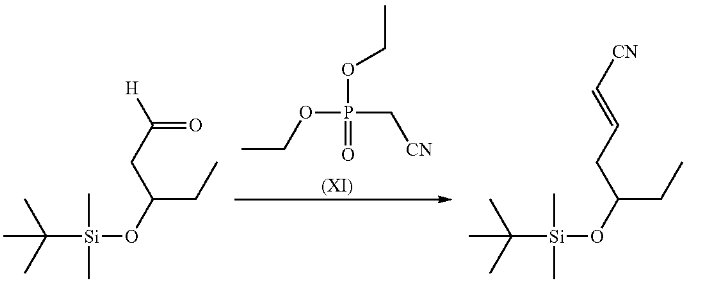

(X)

(XI)

(XII)

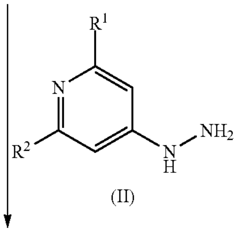

(II)

-continued

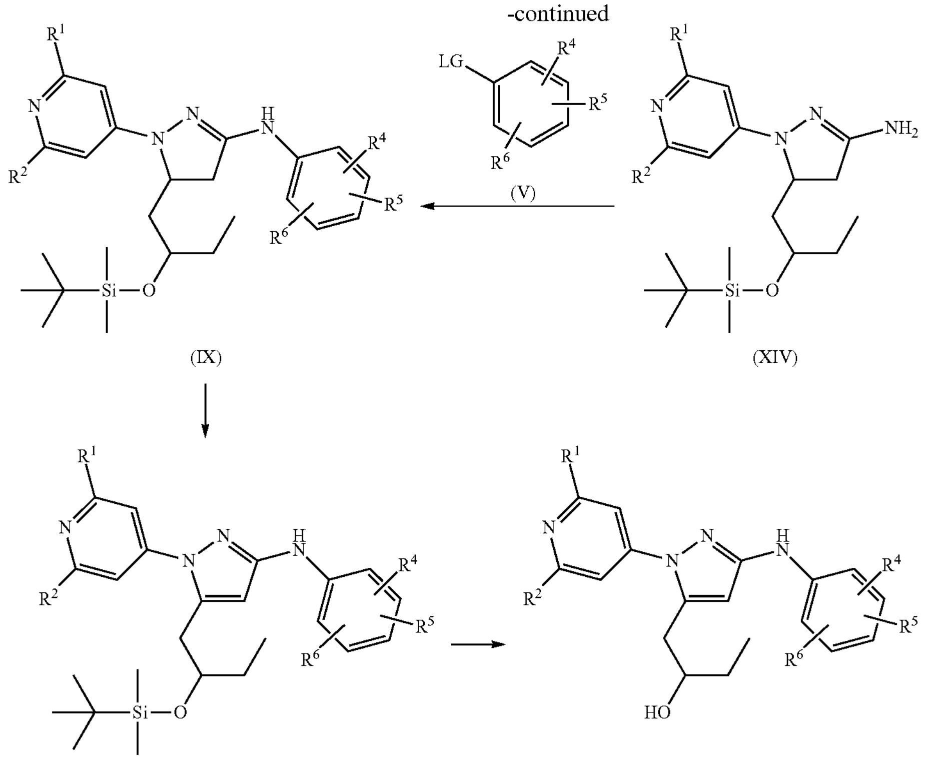

(IX) (XIV)

(XIII) (I-i)

An intermediate of formula (XII) was synthesized by reacting the intermediate of formula (X) (3-[[(1,1-dimethylethyl) dimethylsilyl]oxy]-pentanal), with the cyano derivative of formula (XI) (cyanomethanephosphonic acid diethyl ester) in the presence of a strong inorganic base, such as NaH, or the like and a solvent such as, for example, THF. The intermediate of formula (X) and the intermediate of formula (XI) can be easily prepared by those skilled in the art.

Subsequently, intermediates of the general formula (XIV) can be obtained by a ring closure reaction between an intermediate of formula (XII) and an intermediate of formula (II) under art known conditions. This transformation is typically performed in a protic solvent, in particular an alcohol such as, for example, EtOH in the presence of a strong base such as, for example, sodium ethoxide or metallic sodium. Stirring and elevated temperatures may enhance the rate of the reaction. Intermediates of formula (II) are commercially available or can be easily prepared by those skilled in the art.

In a next step, intermediates of formula (IX) can be prepared in a coupling reaction between an amino derivative of formula (XIV) and an intermediate of formula (V) using transition metal catalysis. LG is defined as a leaving group such as, for example, Cl, Br, I, tosylate, mesylate or triflate, in particular F, Cl, Br or I, more in particular Cl, Br or I, even more in particular Br. Typically a palladium catalyst is used in this type of reaction, for example, $Pd_2(dba)_3$. The palladium catalyzed coupling reaction typically is performed in the presence of a bidentate phosphine ligand such as, for example, [1,1'-binaphthalene]-2,2'-diylbis[diphenylphosphine] (BINAP) or the like and in the presence of a strong inorganic base such as, for example, potassium or sodium tert-butoxide (NaOtBu). This type of reaction can be successfully carried out in an aprotic solvent such as, for example tetrahydrofuran (THF) or the like, at elevated temperatures, in particular between 100° C. and 130° C.

An intermediate of formula (XIII) can be synthesized by reacting an intermediate of formula (IX) in the presence of an oxidation agent such as, for example, $MnO_2$ in the presence of a suitable solvent such as, for example dichloromethane (DCM).

The skilled person will notice that the order of the preceding 2 reaction steps can be switched and that this will also result in an intermediate of formula (XIII).

Finally, the silyl protecting group can be removed at the end of the sequence shown in Scheme 4 in the presence of a desilylating agent such as quaternary ammonium fluoride, preferably tetrabutyl ammonium fluoride (TBAF), using art known conditions. Typically, this kind of reaction is performed in a suitable solvent such as, for example, THF.

By using variants of intermediates of formula (X), that are also commercially available or can be easily prepared by those skilled in the art, analogues of the compounds of formula (I-i) can be prepared in which the hydroxyl group is placed in another position on the alkyl chain or/and in which the alkyl chain ($R^3$) is $C_{1-3}$alkyl.

Pharmacology

The compounds of the present invention were found to be positive allosteric modulators of the α7 nicotinic receptor. The α7 nicotinic receptor (α7 nAChR) belongs to the superfamily of cys-loop, ionotropic ligand-gated ion channels which includes the 5-$HT_3$, $GABA_A$ and glycine receptor families. It is activated by acetylcholine and its breakdown product choline and a major feature of the α7 nAChR is its rapid desensitisation in the persistent presence of agonist. It is the second most abundant nicotinic receptor subtype in the brain and is an important regulator of release of many neurotransmitters. It has a discrete distribution in several brain structures with relevance to attentional and cognitive processes, such as the hippocampus and pre-frontal cortex and has been implicated in a variety of psychiatric and neurological disorders in humans. It is also implicated in the cholinergic inflammatory pathway.

Genetic evidence for its association with schizophrenia is seen in the form of strong linkage between a schizophrenia marker (sensory gating deficit) and the α7 locus on 15q13-14 and polymorphisms in core promoter region of the α7 gene. Pathological evidence points to a loss of α7 immunoreactivity and α-Btx-binding in the hippocampus, frontal and cingulate cortex of schizophrenic brains, in Parkinson's and Alzheimer's disease and paraventricular nucleus and nucleus reuniens in autism.

Pharmacological evidence such as the marked smoking habits of schizophrenics compared to normals have been interpreted as an attempt by the patients to self-medicate to make up for a deficit in α7 nicotinergic transmission. Transient normalization of defects in sensory gating (pre-pulse inhibition, PPI) in both animal models and man upon nicotine administration and temporary restoration of normal sensory gating in schizophrenics when forebrain cholinergic activity low (e.g. stage 2 sleep) have both been interpreted to be the result of transient activation of the α7 nicotinic receptor followed by desensitisation.

Thus there is good reason to suppose that activating the α7 nAChR will have therapeutically beneficial effects for a number of CNS (psychiatric and neurological) disorders.

As already mentioned the α7 nAChR rapidly desensitizes in the persistent presence of the natural transmitter acetylcholine as well as exogenous ligands such as nicotine. In the desensitized state the receptor remains ligand-bound but functionally inactive. This is not so much a problem for natural transmitters such as acetylcholine and choline since these are substrates for very powerful breakdown (acetylcholinesterase) and clearance (choline transporter) mechanisms. These transmitter breakdown/clearance mechanisms are likely to maintain the balance between activatable and desensitized α7 nAChRs in a physiologically useful range. However, synthetic agonists, which are not substrates for the natural breakdown and clearance mechanisms are perceived to have a potential liability both for over-stimulation and also to push the α7 nAChR population equilibrium towards a persistently desensitized state, which is undesirable in disorders in which deficiencies in α7 nAChR expression or function play a role. Agonists by their nature must target the ACh binding pocket which is highly conserved across the different nicotinic receptor subtypes leading to the potential for adverse reactions by non-specific activation of other nicotinic receptor subtypes. Therefore, to avoid these potential liabilities an alternative therapeutic strategy to α7 agonism is to enhance receptor responsiveness to the natural agonists with a positive allosteric modulator (PAM). A PAM is defined as an agent which binds to a site distinct from the agonist binding site, and therefore is not expected to have agonist or desensitization properties, but enhances the responsiveness of the α7 nAChR to the natural transmitter. The value of this strategy is that for a given amount of transmitter the magnitude of α7 nAChR response is increased in the presence of the PAM relative to the level of transmission possible in its absence. So for disorders in which there is a deficit in α7 nAChR protein, the PAM-induced increase in α7 nicotinergic transmission can be beneficial. As a PAM relies on the presence of the natural transmitter the potential for over-stimulation is limited by the breakdown/clearance mechanisms for the natural transmitter.

The compounds of the present invention are classified as type 0-4, based on qualitative kinetic properties, as determined by whole-cell voltage-clamp recordings. This classification is based on the effect of an α7 PAM compound, as described hereinbefore, on the signal elicited by an agonist application. In particular, said agonist is choline at a concentration of 1 mM. In a preferred experimental setting, said α7 PAM compound and choline are simultaneously applied to the cell, as described hereinafter. Desensitization is defined as the closure of the receptor upon activation during the application of the agonist in whole-cell voltage-clamp electrophysiology measurements seen as the reduction of the outward current after initial activation by the agonist.

The definition of the PAM types 0-4 is described hereinafter:

Type 0 compounds minimally enhance the effect size of the current elicited by 1 mM choline.

Type 1 compounds enhance the effect size of the current elicited by 1 mM choline but minimally alter the kinetics of the receptor. In particular, the rate and the extent of desensitization, elicited by the agonist, is not affected. The compound-modulated response to 1 mM choline, therefore, is a close to linear scaling of the 1 mM choline response in absence of the α7 PAM compound.

Type 2 compounds enhance the effect size of the current elicited by 1 mM choline while reducing the rate and/or the extent of desensitization.

Type 3 compounds enhance the effect size of the current elicited by 1 mM choline. When tested at higher concentrations up to 10 μM they completely inhibit desensitization, in particular a 1 mM choline application of 250 milliseconds.

Type 4 compounds allow for an initial desensitization of the receptor followed by a re-opening of the receptor during agonist application. At low-potency concentrations of the α7 PAM compound, the agonist-induced activation, which is followed by desensitization, can still be separated from the compound-induced re-opening as an initial inward current-maximum. At higher potency concentrations of the α7 PAM compound, the re-opening occurs faster than the closure due to desensitization so that the initial current-maximum disappears.

A compound was considered to have interesting PAM-like activity when the potentiation of the peak current was at least 200% compared to the control choline response (=100%). Such compounds are classified as belonging to a particular PAM type in the Experimental Part. Compounds not meeting the condition are not classified as belonging to a particular PAM-type.

It is accordingly an object of the present invention to provide methods of treatment that include administering either a positive allosteric modulator as the only active substance, thus modulating the activity of endogenous nicotinic receptor agonists such as acetylcholine or choline, or administering a positive allosteric modulator together with a nicotinic receptor agonist. In a particular form of this aspect of the invention, the method of treatment comprises treatment with a positive allosteric modulator of the α7 nicotinic receptor as described herein and an α7 nicotinic receptor agonist or partial agonist. Examples of suitable compounds with α7 nicotinic receptor agonistic activity include 1,4-Diazabicyclo[3.2.2]nonane-4-carboxylic acid, 4-bromophenyl ester, monohydrochloride (SSR180711A);

(−)-spiro[1-azabicyclo[2.2.2.]octane-3,5'-oxazolidine]-2'-one;

3-[(2,4-Dimethoxy)Benzylidene]-Anabaseine Dihydrochloride (GTS-21);

[N-[(3R)-1-Azabicyclo[2.2.2]oct-3-yl]-4-chlorobenzamide Hydrochloride] PNU-282987;
nicotine;
varenicline;
MEM3454;
AZD-0328;
MEM63908;
(+)-N-(1-azabicyclo[2.2.2]oct-3-yl)benzo[b]furan-2-carboxamide;
A-582941;
AR-R17779;
TC-1698;
PHA-709829;
tropisetron;
WAY-317538;
EVP-6124; and
TC-5619.

In particular, examples of suitable compounds with α7 nicotinic receptor agonistic activity include 1,4-Diazabicyclo[3.2.2]nonane-4-carboxylic acid, 4-bromophenyl ester, monohydrochloride (SSR180711A); (−)-spiro[1-azabicyclo[2.2.2.]octane-3,5'-oxazolidine]-2'-one; 3-[(2,4-Dimethoxy)Benzylidene]-Anabaseine Dihydrochloride (GTS-21); [N-[(3R)-1-Azabicyclo[2.2.2]oct-3-yl]-4-chlorobenzamide Hydrochloride] PNU-282987; nicotine; varenicline; MEM3454; AZD-0328; and MEM63908.

Positive nAChR modulators of the present invention are useful for treatment or prophylaxis of psychotic disorders, intellectual impairment disorders or diseases or conditions in which modulation of α7 nicotinic receptor activity is beneficial. A particular aspect of the method of the invention is a method of treatment for learning deficit, cognition deficit, attention deficit or memory loss, psychotic disorders, inflammatory diseases, modulation of α7 nicotinic receptor activity is expected to be beneficial in a number of diseases including Alzheimer's disease, Lewy Body Dementia, Attention Deficit Hyperactivity Disorder, anxiety, schizophrenia, mania, manic depression, Parkinson's disease, Huntington's disease, Tourette's syndrome, brain trauma or other neurological, degenerative or psychiatric disorders in which there is loss of cholinergic synapses, including jetlag, nicotine addiction, pain;

a more particular aspect of the method of the invention is a method of treatment for psychotic disorders, intellectual impairment disorders, or inflammatory diseases.

The present invention also relates to a method of treating in a subject the above or below mentioned diseases or disorders, comprising administering to the subject a therapeutically effective amount of a pharmaceutical composition comprising a compound of Formula (I) and a pharmaceutically acceptable carrier.

The compounds may also find therapeutical use as anti-inflammatory medicines because the nicotinic acetylcholine receptor α7 subunit is essential for inhibiting cytokine synthesis by the cholinergic inflammatory pathway. Examples of indications which may be treated by the compounds are endotoxaemia, endotoxic shock, sepsis, rheumatoid arthritis, asthma, multiple sclerosis, psoriasis, urticaria, inflammatory bowel disease, inflammatory bile disease, Crohn's disease, ulcerative colitis, postoperative ileus, pancreatitis, heart failure, acute lung injury and allograft rejection.

The compounds of the invention may find therapeutical use in the following indications as cognition in schizophrenia, cognition in Alzheimer' disease, mild cognitive impairment, Parkinson's disease, attention deficit hyperactivity disorder, ulcerative colitis, pancreatitis, arthritis, sepsis, postoperative ileus and acute lung injury.

In view of the above described pharmacological properties, the compounds according to formula (I) or any subgroup thereof, their, pharmaceutically acceptable addition salts, quaternary amines and stereochemically isomeric forms, may be used as a medicine. In particular, the present compounds can be used for the manufacture of a medicament for treatment or prophylaxis of psychotic disorders, intellectual impairment disorders or diseases or conditions in which modulation of the α7 nicotinic receptor is beneficial.

In view of the above described pharmacological properties, the compounds according to formula (I) or any subgroup thereof, their, pharmaceutically acceptable addition salts, quaternary amines and stereochemically isomeric forms, can be used for treating or preventing psychotic disorders, intellectual impairment disorders or diseases or conditions in which modulation of the α7 nicotinic receptor is beneficial.

In an embodiment the present invention relates to the compounds according to formula (I) for use in treating or preventing psychotic disorders, intellectual impairment disorders or diseases or conditions in which modulation of the α7 nicotinic receptor is beneficial.

In an embodiment the present invention relates to compounds according to formula (I) for use in the treatment or prophylaxis, in particular treatment, of Alzheimer's disease, Lewy Body Dementia, Attention Deficit Hyperactivity Disorder, anxiety, schizophrenia, mania, manic depression, Parkinson's disease, Huntington's disease, Tourette's syndrome, brain trauma or other neurological, degenerative or psychiatric disorders in which there is loss of cholinergic synapses, including jetlag, nicotine addiction, pain, endotoxaemia, endotoxic shock, sepsis, rheumatoid arthritis, asthma, multiple sclerosis, psoriasis, urticaria, inflammatory bowel disease, inflammatory bile disease, Crohn's disease, ulcerative colitis, post-operative ileus, pancreatitis, heart failure, acute lung injury, allograft rejection, cognition in schizophrenia, cognition in Alzheimer' disease, mild cognitive impairment, Parkinson's disease, attention deficit hyperactivity disorder, ulcerative colitis, pancreatitis, arthritis, sepsis, postoperative ileus and acute lung injury.

In an embodiment the present invention relates to the compounds according to formula (I) for use in the treatment or prophylaxis, in particular treatment of psychotic disorders, intellectual impairment disorders or diseases or conditions in which modulation of the α7 nicotinic receptor is beneficial.

In an embodiment the present invention relates to the compounds according to formula (I) for use in the treatment or prophylaxis, in particular treatment, of psychotic disorders, intellectual impairment disorders, or inflammatory diseases.

In an embodiment the present invention relates to the compounds according to formula (I) for treating or preventing, in particular treating, said diseases or conditions.

In view of the utility of the compounds according to formula (I), there is provided a method of treating warm-blooded animals, including humans, suffering from or a method of preventing warm-blooded animals, including humans, to suffer from diseases in which modulation of the α7 nicotinic receptor is beneficial, such as schizophrenia, mania, and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, brain trauma, jetlag, nicotine addiction and pain. Said methods comprise the administration, i.e. the systemic or topical administration, preferably oral administration, of an effective amount of a compound according to formula (I), including all stereochemically isomeric forms thereof, a pharmaceutically acceptable addition salt, a solvate, or a quaternary amine thereof, to warm-blooded animals, including humans.

One skilled in the art will recognize that a therapeutically effective amount of the PAM's of the present invention is the amount sufficient to modulate the activity of the α7 nicotinic receptor and that this amount varies inter alia, depending on the type of disease, the concentration of the compound in the therapeutic formulation, and the condition of the patient. Generally, an amount of PAM to be administered as a therapeutic agent for treating diseases in which modulation of the α7 nicotinic receptor is beneficial, such as schizophrenia, mania, and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, brain trauma, jetlag, nicotine addiction and pain will be determined on a case by case by an attending physician.

Generally, a suitable dose is one that results in a concentration of the PAM at the treatment site in the range of 0.5 nM to 200 μM, and more usually 5 nM to 50 μM. To obtain these treatment concentrations, a patient in need of treatment likely will be administered between 0.01 mg/kg to 2.50 mg/kg body weight, in particular from 0.1 mg/kg to 0.50 mg/kg body weight. The amount of a compound according to the present invention, also referred to here as the active ingredient, which is required to achieve a therapeutically effect will be, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

The present invention also provides compositions for preventing or treating diseases in which modulation of the α7 nicotinic receptor is beneficial, such as schizophrenia, mania, and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, brain trauma, jetlag, nicotine addiction and pain. Said compositions comprising a therapeutically effective amount of a compound according to formula (I) and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences ($18^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound according to formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds according to formula (I) may also be used in combination with other conventional α7 nicotinic receptor agonists or partial agonists, such as for example 1,4-Diazabicyclo[3.2.2]nonane-4-carboxylic acid, 4-bromophenyl ester, monohydrochloride (SSR180711A); (−)-spiro[1-azabicyclo[2.2.2.]octane-3,5'-oxazolidine]-2'-one; 3-[(2,4-Dimethoxy)Benzylidene]-Anabaseine Dihydrochloride (GTS-21); [N-[(3R)-1-Azabicyclo[2.2.2]oct-3-yl]-4-chlorobenzamide Hydrochloride] PNU-282987; nicotine; varenicline; MEM3454; AZD-0328; MEM63908; (+)—N-(1-azabicyclo[2.2.2]oct-3-yl)benzo[b]furan-2-carboxamide; A-582941; AR-R17779; TC-1698; PHA-709829; tropisetron; WAY-317538; EVP-6124; and TC-5619.

The compounds according to formula (I) may also be used in combination with conventional α7 nicotinic receptor agonists, such as for example 1,4-Diazabicyclo[3.2.2]nonane-4-carboxylic acid, 4-bromophenyl ester, monohydrochloride (SSR180711A); (−)-spiro[1-azabicyclo[2.2.2.]octane-3,5'-oxazolidine]-2'-one; 3-[(2,4-Dimethoxy)Benzylidene]-Anabaseine Dihydrochloride (GTS-21); [N-[(3R)-1-Azabicyclo[2.2.2]oct-3-yl]-4-chlorobenzamide Hydrochloride] PNU-282987; nicotine; varenicline; MEM3454; AZD-0328 and MEM63908.

Thus, the present invention also relates to the combination of a compound according to formula (I) and a α7 nicotinic receptor agonist. Said combination may be used as a medicine. The present invention also relates to a product comprising (a) a compound according to formula (I), and (b) a α7 nicotinic receptor agonist, as a combined preparation for simultaneous, separate or sequential use in the treatment of diseases wherein modulation of the α7 nicotinic receptor is beneficial, such as, for example, psychotic disorders, intellectual impairment disorders, or inflammatory diseases. The different drugs may be combined in a single preparation together with pharmaceutically acceptable carriers.

EXAMPLES

Hereinafter, the term "DCM" means dichloromethane; "MeOH" means methanol; "EtOH" means ethanol; "$Pd_2(dba)_3$" means tris(dibenzylideneacetone)dipalladium; "$NH_4OAc$" means ammonium acetate; "BINAP" means [1,1'-binaphthalene]-2,2'-diylbis[diphenylphosphine] (racemic); "NaOtBu" means sodium tert-butoxide; "BDS" means (Base Deactivated Silica); "THF" means tetrahydrofuran; "HPLC" means high-performance liquid chromatography; "iPrOH" means 2-propanol; "NaOEt" means sodium ethoxide; "PDC" means dipyridinium dichromate; "r.t." means room temperature; "HOBT" 1-hydroxy-1H-benzotriazole; "DMSO" means dimethyl sulfoxide; "EDCI" means N-(ethylcarbonimidoyl)-N,N-dimethyl-1,3-propanediamine monohydrochloride; "RP" means reversed phase; "DMAP" means 4-(dimethylamino)pyridine; "min" means minute(s); "TPAP" means tetrapropylammonium perruthenate; "h" means hour(s); "q.s." means quantum sufficit; "I.D." means internal diameter; "$Et_2O$" means diethyl ether; "EtOAc" means ethyl acetate; "$Et_3N$" means triethylamine; "TBAF" means tetrabutylammonium fluoride; "DIPEA" means diisopropylethylamine; "EtOH" means ethanol; "eq" means equivalent; "r.m." means reaction mixture(s); "DIPE" means diisopropyl ether; and "DMF" means N,N-dimethyl formamide;

A. Preparation of the Intermediates

Example A1 a) Preparation of Intermediate 1

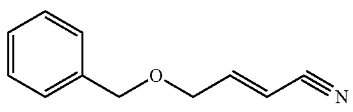

E/Z undetermined

NaH (60%) (8 g, 200 mmol) was stirred in THF (250 ml) under a $N_2$ atmosphere at 0-5° C. A solution of cyanomethanephosphonic acid diethyl ester (35.386 g, 200 mmol) in THF (250 ml) was added dropwise at 0-5° C. and the resulting mixture was stirred for 15 min at 0-5° C. Subsequently, a solution of 2-(phenylmethoxy)acetaldehyde (30 g, 200 mmol) was added drop-wise at 0-5° C. The r.m. was stirred for 1 h at r.t. and was then poured into $H_2O$. The aqueous mixture was extracted with DIPE. The separated organic layer was dried ($MgSO_4$), filtered and concentrated by evaporation. The crude product was purified over silicagel (eluent: DCM). The pure fractions were collected and the solvent was evaporated. Yield: 23 g of intermediate 1 (yield 66%).

b) Preparation of Intermediate 2

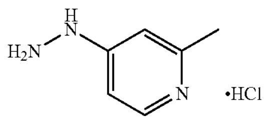

A mixture of 4-chloro-2-methyl-pyridine (10 g, 78.4 mmol), hydrazine hydrate 100% (4.311 g, 86.2 mmol) and iPrOH (30 ml) was reacted for 1 h under a $N_2$ atmosphere at 150° C. Subsequently, the r.m. was diluted with DIPE (30 ml)

and cooled to −15° C. The precipitate was filtered off and dried at 40° C. Yield: 10.7 g of intermediate 2, used as such in the next reaction step.

c) Preparation of Intermediate 3

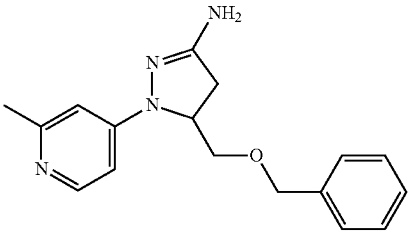 [SMILES: Cc1cc(N2N=C(N)CC2COCc2ccccc2)ccn1]

Sodium (4.48 g, 194.8 mmol, 2.2 eq) was stirred in EtOH (200 ml) at 50° C. under a $N_2$ atmosphere. Intermediate 2 (14.13 g, 88.53 mol, 1 eq) was added at r.t. and the mixture was refluxed for 30 min. Intermediate 1 (23 g, 132.8 mmol, 1.5 eq) was then added at r.t. and the r.m. was stirred overnight at 50° C. Subsequently, the solvent was evaporated, $H_2O$ was added to the residue and the aqueous mixture was extracted with EtOAc. The separated organic layer was dried ($MgSO_4$), filtered and the solvent was evaporated. The product was crystallized from $Et_2O$ (q.s.). The crystals were filtered off and dried. Yield: 18.6 g of intermediate 3 (yield 71%).

d) Preparation of Intermediate 4

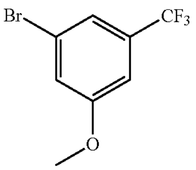

3-Methoxy-5-(trifluoromethyl)benzenamine (20 g, 104.6 mmol) was added portion-wise to a cooled solution of $NaNO_2$ (7.392 g, 107.1 mmol) in $H_2SO_4$ (74 ml) and $CH_3COOH$ (88 ml). This mixture was added dropwise to a vigorously stirred solution of CuBr (18 g, 62.8 mmol) in 48% HBr (200 ml) at 0° C. The r.m. was stirred for 45 min at r.t. and was then poured into ice-water. This aqueous mixture was extracted with DCM. The separated organic layer was dried ($MgSO_4$), filtered and the solvent was evaporated at low temperature. The residue was stirred in a $NaHCO_3$ solution and extracted with DIPE. The separated organic layers was dried ($MgSO_4$), filtered and the solvent was evaporated. Yield: 12.7 g of intermediate 4 (yield 48%).

e) Preparation of Intermediate 5

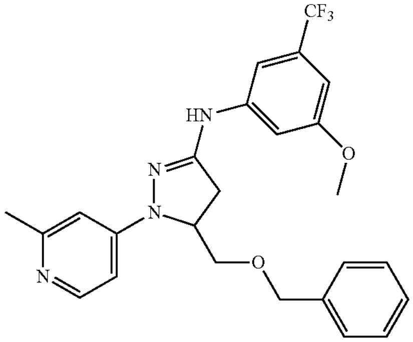 [SMILES: COc1cc(NC2=NN(c3ccnc(C)c3)C(COCc3ccccc3)C2)cc(C(F)(F)F)c1]

Intermediate 3 (5 g, 16.87 mmol) was stirred in THF (100 ml). Intermediate 4 (6.607 g, 25.9 mmol), $Pd_2(dba)_3$ (1.4 g), BINAP (1.9 g) and NaOtBu (4 g) were added to this mixture. The r.m. was stirred for 2 h in the microwave at 110° C. Subsequently, EtOAc (800 ml) and brine (200 ml) were added and the mixture was stirred. The organic layer was separated, dried ($MgSO_4$), filtered, and the solvent was evaporated. The residue was crystallized from $CH_3CN$. The product was filtered off and dried, yielding 5.7 g of intermediate 5. When desired, an additional amount of product can be obtained by evaporation of the filtrate and purification of the obtained residue (by e.g. reversed-phase HPLC).

Example A2 a) Preparation of Intermediate 6

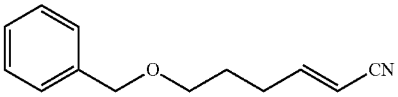

E/Z undetermined

NaH (60%) (7 g, 181.8 mmol) was washed with heptanes (q.s.) and stirred in THF (150 ml) under a $N_2$ atmosphere at 0-5° C. Cyanomethanephosphonic acid diethyl ester (32.202 g, 181.8 mmol) was dissolved in THF (150 ml) and this solution was added drop-wise at 0-5° C. The mixture was stirred for 15 min. Subsequently, 4-(phenylmethoxy)-butanal (32.4 g, 181.8 mmol) was dissolved in THF (100 ml) and this solution was added drop-wise at 0-5° C. The r.m. was stirred for 1 h at r.t. and was then poured into $H_2O$. The aqueous mixture was extracted with DIPE. The organic layer was separated, dried ($MgSO_4$), filtered and concentrated by evaporation. The residue was purified by HPLC, yielding 18.6 g of intermediate 6 (yield 51%).

b) Preparation of Intermediate 7

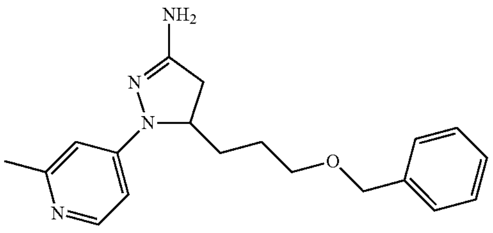 [SMILES: Cc1cc(N2N=C(N)CC2CCCOCc2ccccc2)ccn1]

A 21% solution of NaOEt in EtOH (35 ml) was stirred in EtOH (110 ml) under a $N_2$ atmosphere. Intermediate 2 (10.4 g, 53.04 mmol) was added portionwise at r.t. and the mixture was stirred for 1 h at 70° C. Then the mixture was cooled and intermediate 6 (13.563 g, 67.39 mmol) was added drop-wise. The r.m. was stirred for 2 h at r.t. and then for 2 days at 45° C. Subsequently, the r.m. was filtered and the filtrated was concentrated by evaporation. The residue was dissolved in EtOAc (800 ml) and this solution was washed with brine (200 ml). The organic layer was dried ($MgSO_4$), filtered and concentrated by evaporation. The residue was purified by column chromatography over silicagel (eluent: DCM/MeOH from 98/2 to 85/15). The desired fractions were collected and the solvent was evaporated. Yield: 2.6 g of crude intermediate 7, used as such in the next reaction steps. More product can be obtained by further purification of the less pure fractions by RP HPLC(RP Shandon Hyperprep C18 BDS—8 μm, 250 g, I.D. 5 cm; mobile phase: 0.25% $NH_4HCO_3$ solution in water; MeOH+$CH_3CN$). The desired fractions were collected and worked-up, yielding 5 g of intermediate 7.

c) Preparation of Intermediate 15

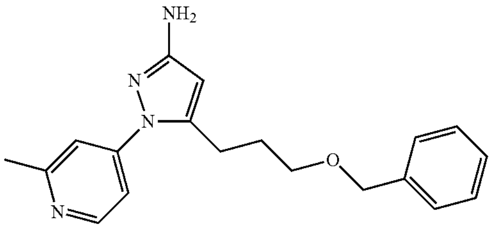 [SMILES: Cc1cc(-n2nc(N)cc2CCCOCc2ccccc2)ccn1]

A mixture of Intermediate 7 (8.2 g, 25.275 mmol) and $MnO_2$ (21.974 g, 252.754 mmol) in DCM was stirred at r.t. for 16 h. The r.m. was then filtered over diatomaceous earth and the solvent was evaporated. The residue was purified by column chromatography over silicagel (DCM/MeOH from 98/2 to 85/15). The desired fractions were collected and the solvent was evaporated. The residue was further purified by RP HPLC(RP Shandon Hyperprep C18 BDS—8 μm, 250 g, I.D. 5 cm; mobile phase: 0.25% $NH_4HCO_3$ solution in $H_2O$; MeOH+$CH_3CN$). The desired fractions were collected and worked-up. Yield: 980 mg of intermediate 15 (yield 12%).

Example A3 a) Preparation of Intermediate 8

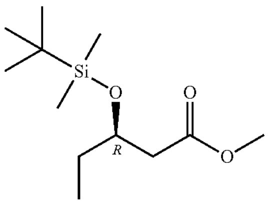

A mixture of (3R)-3-hydroxypentanoic acid methyl ester (20 g, 151.33 mmol), 1H-imidazole (22.66 g, 332.93 mmol), DMAP (1.85 g, 15.13 mmol) and DMF (800 ml) was stirred at 0° C. Chloro(1,1-dimethylethyl)dimethylsilane (27.37 g, 181.60 mmol) was added and the mixture was stirred overnight at r.t. The solvent was evaporated and $H_2O$ was added to the residue. The aqueous mixture was extracted with DIPE. The separated organic layer was dried ($MgSO_4$), filtered and the solvent was evaporated. Yield: 24 g of intermediate 8 (yield 64%; R-enantiomer).

b) Preparation of Intermediate 9

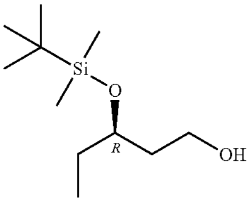

$LiBH_4$ (2.14 g, 97.40 mmol) was stirred in THF (70 ml) at r.t. Intermediate 8 (24 g, 97.39 mmol) in THF (70 ml) was added over 5 min and the r.m. was heated to reflux temperature and refluxed for 2 h. Subsequently, $Et_2O$ (200 ml) and a saturated $NH_4Cl$ solution were added at 0° C. The r.m. was stirred for 30 min at 0° C. The organic layer was separated, dried ($MgSO_4$), filtered and the solvent was evaporated. The residue was dissolved in DCM and this solution was washed with $H_2O$. The organic layer was dried ($MgSO_4$), filtered and the solvent was evaporated. Yield: 15 g of intermediate 9 (yield 71%; R-enantiomer).

c) Preparation of Intermediate 10

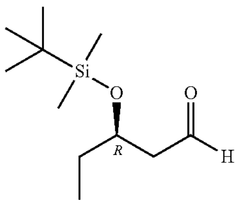

A mixture of intermediate 9 (14.5 g, 66.40 mmol), N-methylmorpholine-N-oxide (12.5 g, 103.82 mmol), molecular sieves powder (33.4 g) and DCM (700 ml) was stirred under a $N_2$ atmosphere for 30 min at r.t. TPAP (1.25 g) was added and the mixture was stirred for 1 h. The mixture was filtered over a glass filter containing a layer of silicagel and a top-layer of diatomaceous earth. The filter was washed with DCM. The filtrate was evaporated. Yield: 10.5 g of intermediate 10 (yield 73%; R-enantiomer).

d) Preparation of Intermediate 11

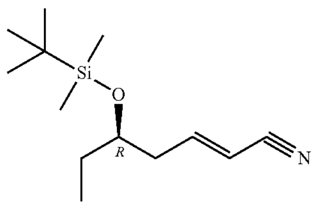

E/Z undetermined

NaH 60% (2.03 g, 50.83 mmol) was washed with heptanes and was then stirred in THF (100 ml) at 0-5° C. under a $N_2$ atmosphere. A solution of cyanomethanephosphonic acid diethyl ester (9.005 g, 50.83 mmol) in THF (100 ml) was added drop-wise at 0-5° C. and the mixture was stirred for 15 min. Subsequently, a solution of intermediate 10 (11 g, 50.83 mmol) in THF (100 ml) was added drop-wise at 0-5° C. and the mixture was stirred for 1 h at r.t. $H_2O$ was added and the product was extracted with DIPE. The separated organic layer was dried ($MgSO_4$), filtered and the solvent was evaporated. The residue was purified on silicagel (eluent: DCM). The desired fractions were collected and the solvent was evaporated. Yield: 9.4 g of intermediate 11 (yield 77%; R-enantiomer).

e) Preparation of Intermediate 12

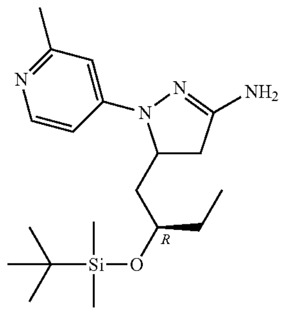

Na (1.35 g, 58.5 mmol) was dissolved in EtOH (50 ml) at 50° C. under a $N_2$ atmosphere. Intermediate 2 (3.735 g, 23.4 mmol) was added portion-wise at r.t. The mixture was stirred and refluxed for 30 min, and was then cooled to r.t. Intermediate 11 (8.4 g, 35.08 mmol) was added drop-wise and the r.m. was stirred overnight at 50° C. Subsequently, the solvent was evaporated and $H_2O$ and EtOAc were added to the residue. The organic layer was separated, dried ($MgSO_4$), filtered and the solvent was evaporated. The residue was purified by RP HPLC (Shandon Hyperprep® C18 BDS 8 nm, 250 g, I.D. 5 cm; Mobile phase: 90% of a 0.5% $NH_4OAc$ solution in water+10% $CH_3CN$; $CH_3CN$). The desired fractions were collected and the solvent was evaporated. DCM was added and the solution was washed with a $NaHCO_3$ solution. The organic layer was dried ($MgSO_4$), filtered and the solvent was evaporated. Yield: 1.5 g of intermediate 12 (yield 12%).

f) Preparation of Intermediate 13

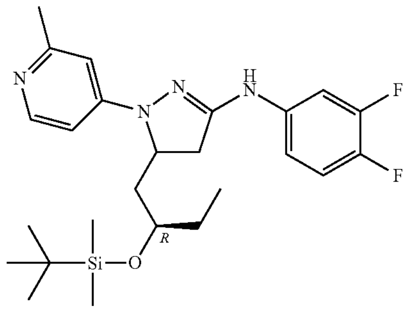

A mixture of intermediate 12 (700 mg, 1.93 mmol), 4-bromo-1,2-difluorobenzene (558.87 mg, 2.90 mmol), $Pd_2(dba)_3$ (196 mg), BINAP (266 mg) and NaOtBu (560 mg) in THF (5 ml) was stirred for 2 h at 110° C. under microwave irradiation. The mixture was evaporated, washed with $H_2O$ and extracted with DCM. The separated organic layer was dried ($MgSO_4$), filtered and the solvent was evaporated. The product was purified on silicagel (eluent: DCM/MeOH($NH_3$) from 90/10 to 80/20). The desired fractions were collected and the solvent was evaporated. Yield: 1 g of intermediate 13 (quantitative yield).

g) Preparation of Intermediate 14

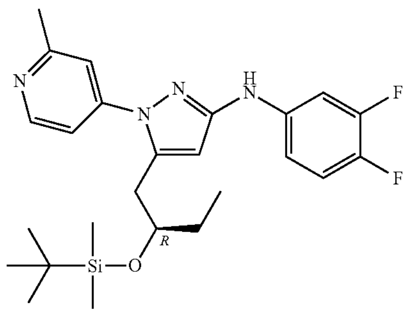

Intermediate 13 (1 g, 2.107 mmol) was stirred in DCM (400 ml) at r.t. $MnO_2$ (2.5 g) was added and the mixture was stirred for 2 h. Subsequently, the mixture was filtered over diatomaceous earth and the filtrate was evaporated. The product was purified by column chromatography over silicagel (eluent: DCM/MeOH($NH_3$) from 99/1 to 98/2). The pure fractions were collected and the solvent was evaporated. Yield: 440 mg of intermediate 14 (yield 44%).

Example A4

Preparation of Intermediate 16

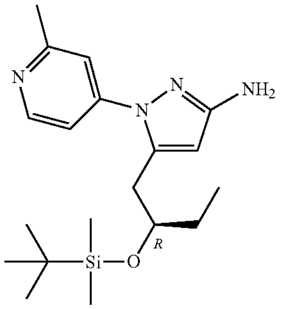

Intermediate 12 (8 g, 22.063 mmol) was stirred in DCM (q.s.). $MnO_2$ (20 g) was added portion-wise and the r.m. was stirred for 2 h at r.t. Then the r.m. was filtered over diatomaceous earth and the filtrate was concentrated by evaporation. The residue was purified by RP Preparative HPLC (Shandon Hyperprep® C18 BDS 8 μm, 250 g, I.D. 5 cm; Mobile phase: 0.25% $NH_4HCO_3$ solution in $H_2O$, MeOH+$CH_3CN$). The desired fractions were collected and the solvent was evaporated, yielding 3 g of intermediate 16 (yield 38%).

B. Preparation of the Compounds

Example B1 a) Preparation of Compound 1

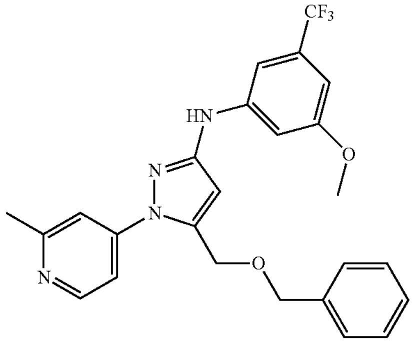 [SMILES: COc1cc(Nc2cc(COCc3ccccc3)n(-c3ccnc(C)c3)n2)cc(C(F)(F)F)c1]

Intermediate 5 (5.7 g, 12.12 mmol) was stirred in DCM (1 l). $MnO_2$ (17 g) was added and the r.m. was stirred at r.t. for 6 h. Subsequently, the mixture was filtered over diatomaceous earth and the filtrate was concentrated by evaporation. The residue was purified by column chromatography over silicagel (eluent: DCM/MeOH 98/2). The desired fractions were collected and the solvent was evaporated. Yield: 4.1 g of compound 1 (yield 72%).

b) Preparation of Compound 2

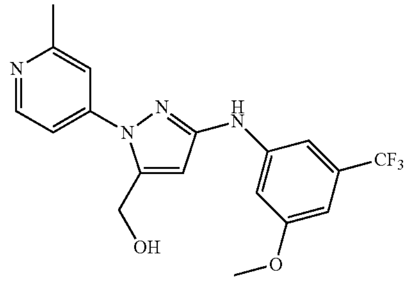 [SMILES: COc1cc(Nc2cc(CO)n(-c3ccnc(C)c3)n2)cc(C(F)(F)F)c1]

Compound 1 (4 g, 8.54 mmol) was stirred in DCM (250 ml) at −10° C. under $N_2$ atmosphere. A 1 M $BBr_3$ solution in DCM (11 ml) was added drop-wise and the r.m. was stirred for 30 min. Subsequently, an additional amount of 1 M $BBr_3$ solution in DCM (3 ml) was added and the r.m. was stirred for 30 min. A saturated $NaHCO_3$ solution (100 ml) was added and the mixture was stirred. The organic layer was separated and purified by column chromatography over silicagel (eluent: DCM/MeOH from 100/0 to 90/10). The desired fractions were collected and the solvent was evaporated. Yield: 3.2 g of compound 2.

c) Preparation of Compound 3

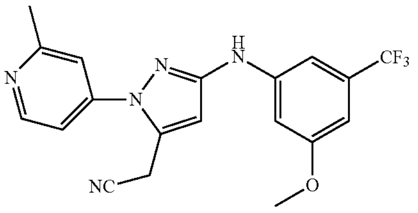 [SMILES: COc1cc(Nc2cc(CC#N)n(-c3ccnc(C)c3)n2)cc(C(F)(F)F)c1]

Compound 2 (3.2 g, 8.46 mmol) and $Et_3N$ (3 g) were stirred in THF (400 ml). Mesyl chloride (1.453 g, 12.69 mmol) was added drop-wise. This mixture was stirred for 1 h at r.t. Subsequently, an additional amount of $Et_3N$ (1 g) and mesyl chloride (1 g) was added and the mixture was stirred for 1 h at r.t. Finally, more $Et_3N$ (1 g) and mesyl chloride (1 g) was added and again the mixture was stirred for 1 h at r.t. Then DMSO (200 ml) and NaCN (4 g) were added and the r.m. was stirred at reflux temperature for 1 h under a $N_2$ flow. Subsequently, the THF was removed by evaporation at 70° C., and the mixture was concentrated by evaporation. The residue was stirred in EtOAc and this mixture was washed with $H_2O$. The organic layer was dried ($MgSO_4$), filtered and concentrated by evaporation. The residue was purified by column chromatography (eluent: DCM/MeOH 95/5). The desired fractions were collected and the solvent was evaporated, yielding 2.7 g of the crude product. This crude product was crystallized from ether and the product filtered off. Yield: 2.0 g of compound 3.

d) Preparation of Compound 4

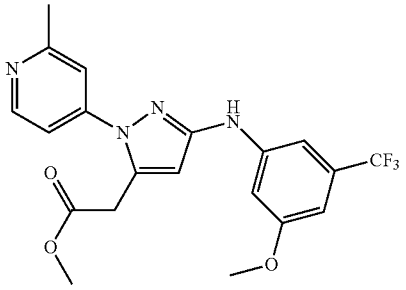 [SMILES: COC(=O)Cc1cc(Nc2cc(OC)cc(C(F)(F)F)c2)nn1-c1ccnc(C)c1]

Compound 3 (1.3 g, 3.35 mmol) and HCl 37% (200 ml) were stirred for 3 h at 70° C. Then the mixture was concentrated by evaporation. The residue was stirred in DIPE and the precipitate was filtered off. The precipitate was stirred in MeOH (200 ml) and HCl (5 ml). The r.m. was neutralized with DIPEA (q.s.) on a cooling bath. Subsequently, the mixture was concentrated by evaporation and the residue was dissolved in DCM. This solution was washed with $H_2O$ (q.s.), dried ($MgSO_4$), filtered and concentrated by evaporation. The residue was purified by column chromatography over silica gel (eluent: DCM/MeOH 95/5). The desired fractions were collected and the solvent was evaporated. Yield: 1 g of compound 4 (yield 71%).

e) Preparation of Compound 5

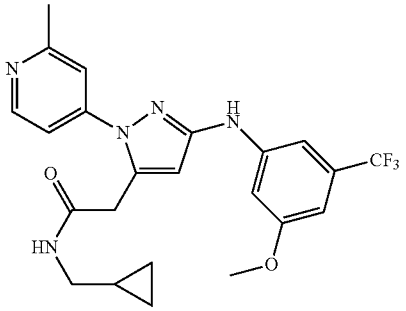 [SMILES: COc1cc(Nc2cc(CC(=O)NCC3CC3)n(-c3ccnc(C)c3)n2)cc(C(F)(F)F)c1]

Compound 4 (0.2 g, 0.476 mmol) was stirred in cyclopropanemethanamine for 6 h at r.t. Then the mixture was concentrated by evaporation and the residue was dissolved in DCM. This organic solution was washed with $H_2O$, dried ($MgSO_4$), filtered and concentrated by evaporation. The residue was purified by RP HPLC (RP Shandon Hyperprep C18 BDS—8 μm, 250 g, I.D. 5 cm; mobile phase: 0.25% $NH_4HCO_3$ solution in $H_2O$; MeOH+$CH_3CN$). The desired fractions were collected and worked-up. Yield: 0.109 g of compound 5 (yield 50%).

Example B2 a) Preparation of Compound 6

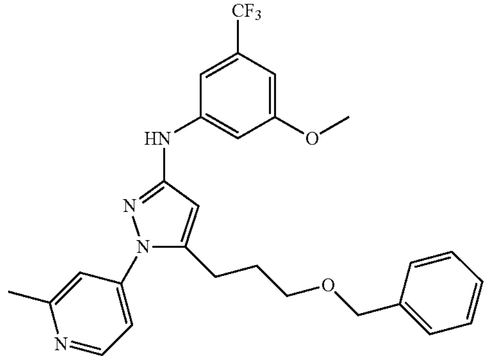 [SMILES: COc1cc(Nc2cc(CCCOCc3ccccc3)n(-c3ccnc(C)c3)n2)cc(C(F)(F)F)c1]

Intermediate 15 (0.98 g, 3.04 mmol) was stirred in THF (20 ml). Intermediate 4 (1.163 g, 4.56 mmol), $Pd_2(dba)_3$ (360 mg), BINAP (480 mg) and NaOtBu (960 mg) were added and the r.m. was stirred for 2 h at 110° C. under microwave irradiation. Subsequently, EtOAc (200 ml) and brine (40 ml) were added to the r.m. and the mixture was stirred. The organic layer was separated, dried ($MgSO_4$), filtered and concentrated by evaporation. The residue was purified by column chromatography over silicagel (eluent: DCM/MeOH from 100/0 to 90/10). The desired fractions were collected and the solvent was evaporated. Yield: 2.2 g of compound 6 (quantitative yield).

b) Preparation of Compound 7

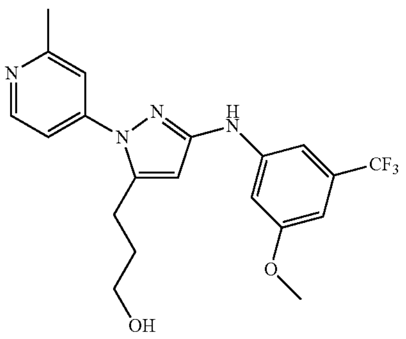 [SMILES: COc1cc(Nc2cc(CCCO)n(-c3ccnc(C)c3)n2)cc(C(F)(F)F)c1]

MeOH (150 ml) was added to Pd/C 10% (1 g) under a $N_2$ atmosphere. Compound 6 (2.2 g, 4.43 mmol) was added and the mixture was stirred under a $H_2$ atmosphere at 50° C. until 1 eq of hydrogen was absorbed. Subsequently, the mixture was filtered over diatomaceous earth. The product was purified by column chromatography over silicagel (DCM/MeOH from 100/0 till 90/10). The desired fractions were collected and the solvent was evaporated. Yield: 105 mg of compound 7 (yield 6%).

c) Preparation of Compound 8

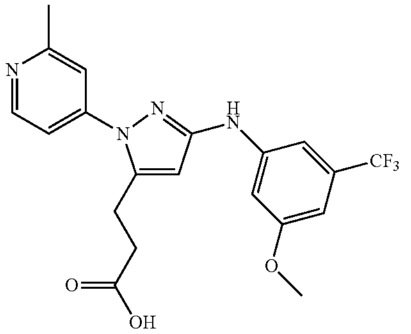 [SMILES: COc1cc(Nc2cc(CCC(=O)O)n(-c3ccnc(C)c3)n2)cc(C(F)(F)F)c1]

Compound 7 (105 mg, 0.26 mmol) was dissolved in DMF (10 ml). This solution was cooled at 0° C. and PDC (116.64 mg, 0.31 mmol) and 98% $H_2SO_4$ (0.05 ml) were added. The r.m. was stirred for 16 h at r.t. Subsequently, the mixture was poured into $H_2O$ and was extracted with EtOAc. The separated organic layer was dried ($MgSO_4$), filtered and concentrated by evaporation. Yield: 129 mg of compound 8.

d) Preparation of Compound 9

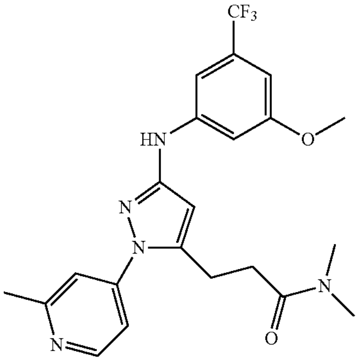

Compound 8 (230 mg, 0.55 mmol) was dissolved in DMF (10 ml). Dimethylamine hydrochloride (178.46 mg, 2.19 mmol), HOBT (221.78 mg, 1.64 mmol), EDCI (254.80 mg, 1.64 mmol) and DIPEA (282.85 mg, 2.19 mmol) were added to the solution. The r.m. was stirred overnight at r.t. and was then poured in $H_2O$ and extracted with DCM (2×20 ml). The combined organic layers were washed with brine, dried ($MgSO_4$), filtered and the solvent was evaporated. The residue was purified by RP HPLC (RP Shandon Hyperprep C18 BDS—8 μm, 250 g, I.D. 5 cm; mobile phase: 0.25% $NH_4HCO_3$ solution in $H_2O$; MeOH+$CH_3CN$). The desired fractions were collected and worked-up. Yield: 31.8 mg of compound 9 (yield 13%).

Example B3

Preparation of Compound 10

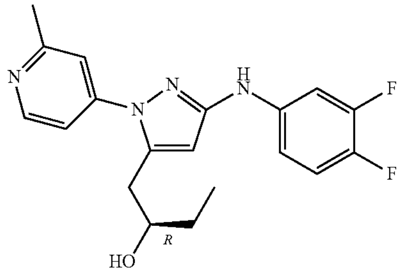

A mixture of intermediate 14 (410 mg, 0.867 mmol) and a 1 M TBAF solution in THF was stirred for 2 h at r.t. A saturated $NH_4Cl$ solution was added and the mixture was extracted with EtOAc. The separated organic layer was dried ($MgSO_4$), filtered and the solvent was evaporated. The residue was purified by column chromatography over silicagel (eluent: DCM/MeOH 96/4). The desired fractions were collected and the solvent was evaporated. The residue was taken up in a 1 N HCl solution and this solution was washed with DCM. The water layer was alkalized and extracted with DCM. The organic layer was dried (Extrelute®), filtered and the solvent was evaporated. Yield: 116 mg of compound 10 (yield 37%).

Example B4 a) Preparation of Compound 11

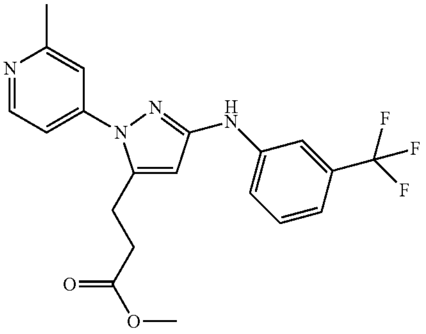 [SMILES: COC(=O)CCc1cc(Nc2cccc(C(F)(F)F)c2)nn1-c1ccnc(C)c1]

A mixture of compound 32 (prepared by analogy to the protocol described in Example B2.b) (80 mg, 0.213 mmol) was dissolved in DMF (10 ml). The solution was cooled to 0° C. and PDC (95.956 mg, 0.255 mmol) and 98% $H_2SO_4$ (0.05 ml) was added. The r.m. was stirred at r.t. for 2 h (LCMS showed that crude compound 12 was formed). The mixture was evaporated and the residue was purified by column chromatography over silicagel (eluent: DCM/MeOH from 98/2 to 85/15). The desired fractions were collected and the solvent was evaporated. The product was converted to the methyl ester. Yield: 119 mg of compound 11.

b) Preparation of Compound 12

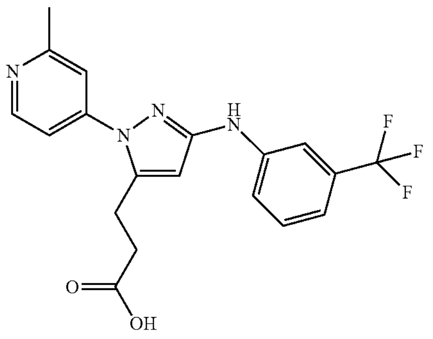 [SMILES: Cc1cc(-n2nc(Nc3cccc(C(F)(F)F)c3)cc2CCC(=O)O)ccn1]

A mixture of compound 11 (119 mg, 0.294 mmol) was dissolved in MeOH (10 ml) and $H_2O$ (10 ml). LiOH (30 mg, 0.214 mmol) was added to the solution and the r.m. was stirred for 1 h at r.t. The mixture was worked-up, yielding 159 mg of compound 12.

Example B5

Preparation of Compound 13

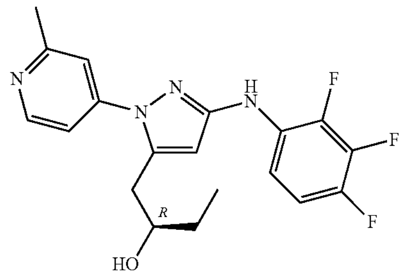

A mixture of intermediate 16 (320 mg, 0.887 mmol), 1-bromo-2,3,4-trilfluorobenzene (280.86 mg, 1.331 mmol), $Pd_2(dba)_3$ (90 mg), BINAP (120 mg) and NaOtBu (257 mg) in THF (15 ml) was stirred for 1 h at 110° C. under microwave irradiation. This mixture was then poured into a saturated $NH_4Cl$ solution, EtOAc was added and the r.m. was stirred at r.t. The organic layer was separated, dried ($MgSO_4$), filtered, and concentrated by evaporation. The residue was dissolved in THF (50 ml) and a 1 M TBAF solution in THF (10 ml) was added. The r.m. was stirred for 2 h at r.t. Subsequently, a saturated $NH_4Cl$ solution (75 ml) was added. The mixture was stirred and extracted with EtOAc. The separated organic layer was dried ($MgSO_4$), filtered and concentrated by evaporation. The residue was dissolved in EtOAc and this solution was washed with $H_2O$ (3×), dried ($MgSO_4$) and concentrated again by evaporation. The residue was further purified by RP Preparative HPLC (RP Vydac Denali C18—10 μm, 250 g, I.D. 5 cm; mobile phase: 0.25% $NH_4HCO_3$ solution in $H_2O$; MeOH+$CH_3CN$). The desired fractions were collected and worked-up. Yield: 102 mg of compound 13 (yield 31%; R enantiomer).

Compounds 1 to 124 in tables 1a, 1b, 1c, 1d, 1e and 1f list the compounds that were prepared by analogy to one of the above Examples. In case no salt form is indicated, the compound was obtained as a free base. 'Pr.' refers to the Example number according to which protocol the compound was synthesized. 'Co. No.' means compound number.

In order to obtain the HCl salt forms, several procedures known to those skilled in the art were used.

TABLE 1a

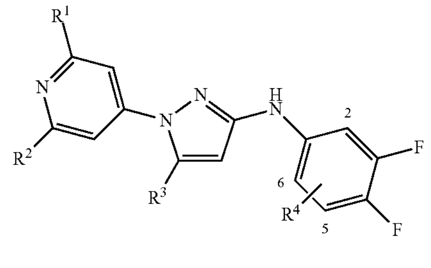

| Co. No. | Pr. | $R^1$ | $R^2$ | $R^3$ | $R^4$ | Stereochemistry and salt forms |
|---|---|---|---|---|---|---|
| 14 | B1.a | $CH_3$ | H | $CH_3$ | H | |
| 15 | B1.b | $CH_3$ | H | $CH_2OH$ | H | |
| 16 | B2.b | $CH_3$ | H | 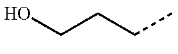 | H | |

TABLE 1a-continued
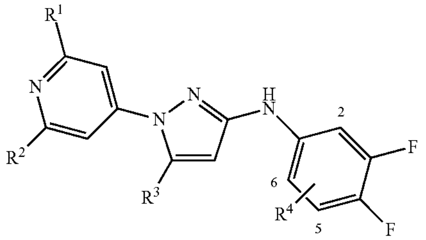
| Co. No. | Pr. | $R^1$ | $R^2$ | $R^3$ | $R^4$ | Stereochemistry and salt forms |
|---|---|---|---|---|---|---|
| 10 | B3 | $CH_3$ | H | 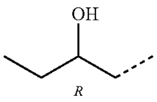 | H | R-enantiomer |
| 17 | B5 | $CH_3$ | H | 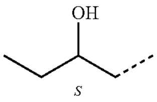 | H | S-enantiomer |
| 18 | B5 | $CH_3$ | H | 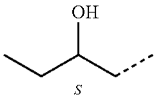 | 2-F | S-enantiomer |
| 13 | B5 | $CH_3$ | H | 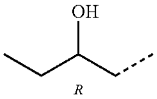 | 2-F | R-enantiomer |
| 19 | B5 | $CH_3$ | H | 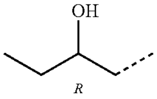 | 5-F | R-enantiomer |
| 20 | B5 | $CH_3$ | H | 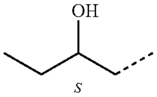 | 5-F | S-enantiomer |
| 21 | B5 | $CH_3$ | H | 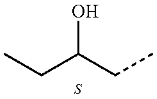 | 6-F | S-enantiomer |
| 22 | B1.c | $CH_3$ | H | 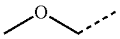 | H | |
| 23 | B1.c | $CH_3$ | H | 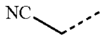 | H | |
| 24 | B1.d | $CH_3$ | H | 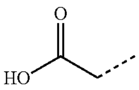 | H | |
| 25 | B2.c | $CH_3$ | H | 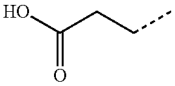 | H | |
| 26 | B1.d | $CH_3$ | H | 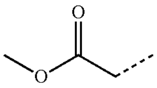 | H | .HCl |

TABLE 1a-continued
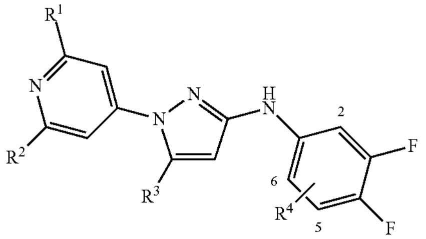
| Co. No. | Pr. | $R^1$ | $R^2$ | $R^3$ | $R^4$ | Stereochemistry and salt forms |
|---|---|---|---|---|---|---|
| 27 | B1.e | $CH_3$ | H | 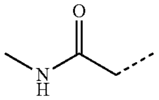 | H | |
| 28 | B1.e | $CH_3$ | H | 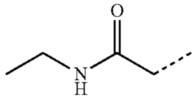 | H | |
| 29 | B1.e | $CH_3$ | H | 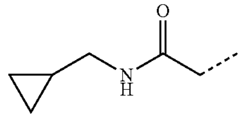 | H | |
| 30 | B2.d | $CH_3$ | H | 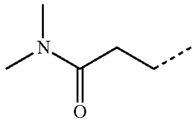 | H | |
| 31 | B1.a | $CH_3$ | H | 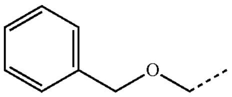 | H | |
| 32 | B1.a | $CH_3$ | H | 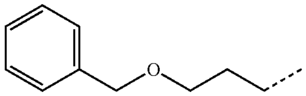 | H | |
TABLE 1b
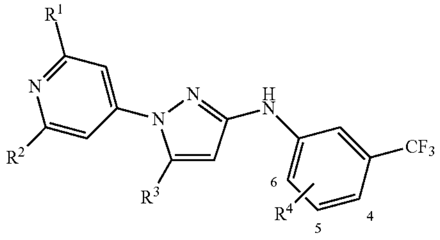
| Co. No. | Pr. | $R^1$ | $R^2$ | $R^3$ | $R^4$ | Stereochemistry and salt forms |
|---|---|---|---|---|---|---|
| 33 | B1.b | $CH_3$ | H | $CH_2OH$ | H | |
| 2 | B1.b | $CH_3$ | H | $CH_2OH$ | 5-$OCH_3$ | |
| 34 | B2.b | $CH_3$ | H | 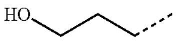 | H | |
| 7 | B2.b | $CH_3$ | H | 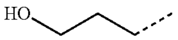 | 5-$OCH_3$ | |

TABLE 1b-continued
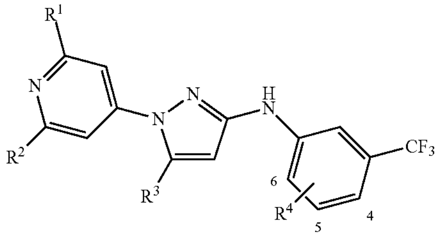
| Co. No. | Pr. | $R^1$ | $R^2$ | $R^3$ | $R^4$ | Stereochemistry and salt forms |
|---|---|---|---|---|---|---|
| 35 | B3 | $CH_3$ | H | 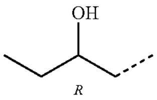 | H | R-enantiomer |
| 36 | B3 | $CH_3$ | H | 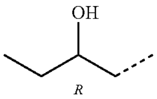 | 5-$OCH_3$ | R-enantiomer |
| 37 | B5 | $CH_3$ | H | 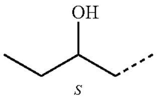 | H | S-enantiomer |
| 38 | B5 | $CH_3$ | H | 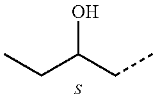 | 4-$OCH_3$ | S-enantiomer |
| 39 | B5 | $CH_3$ | H | 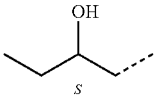 | 5-$OCH_3$ | S-enantiomer |
| 40 | B1.c | $CH_3$ | H | 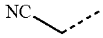 | H | |
| 3 | B1.c | $CH_3$ | H | 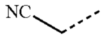 | 5-$OCH_3$ | |
| 8 | B2.c | $CH_3$ | H | 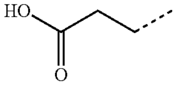 | 5-$OCH_3$ | |
| 12 | B4.b | $CH_3$ | H | 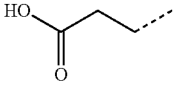 | H | |
| 41 | B1.d | $CH_3$ | H | 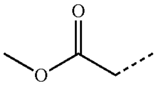 | H | |
| 4 | B1.d | $CH_3$ | H | 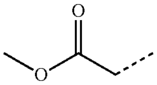 | 5-$OCH_3$ | |
| 11 | B4.a | $CH_3$ | H | 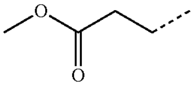 | H | |
| 42 | B1.e | $CH_3$ | H | 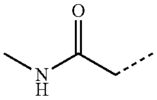 | H | |

TABLE 1b-continued
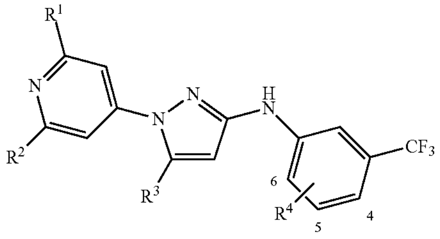
| Co. No. | Pr. | $R^1$ | $R^2$ | $R^3$ | $R^4$ | Stereochemistry and salt forms |
|---|---|---|---|---|---|---|
| 43 | B1.e | $CH_3$ | H | 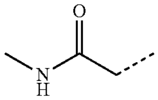 | 5-$OCH_3$ | |
| 44 | B1.e | $CH_3$ | H | 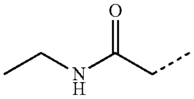 | H | |
| 45 | B1.e | $CH_3$ | H | 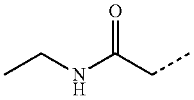 | 5-$OCH_3$ | |
| 46 | B1.e | $CH_3$ | H | 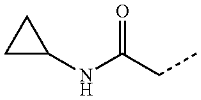 | 5-$OCH_3$ | |
| 47 | B1.e | $CH_3$ | H | 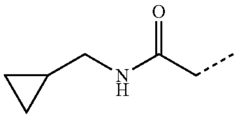 | H | |
| 5 | B1.e | $CH_3$ | H | 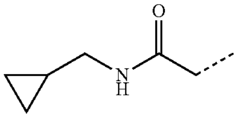 | 5-$OCH_3$ | |
| 48 | B1.e | $CH_3$ | H | 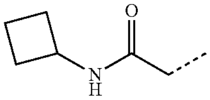 | 5-$OCH_3$ | |
| 49 | B2.d | $CH_3$ | H | 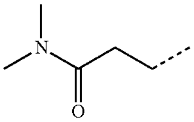 | H | |
| 9 | B2.d | $CH_3$ | H | 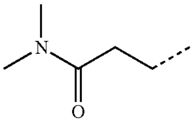 | 5-$OCH_3$ | |
| 50 | B1.a | $CH_3$ | H | 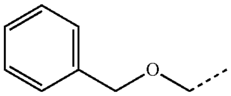 | H | |
| 1 | B1.a | $CH_3$ | H | 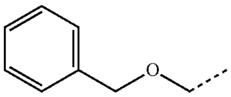 | 5-$OCH_3$ | |

TABLE 1b-continued
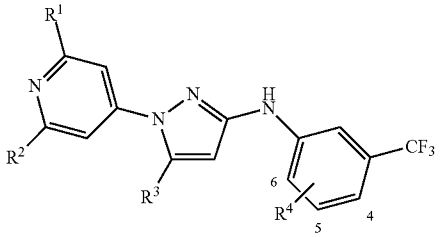
| Co. No. | Pr. | $R^1$ | $R^2$ | $R^3$ | $R^4$ | Stereochemistry and salt forms |
|---|---|---|---|---|---|---|
| 51 | B2.a | $CH_3$ | H | 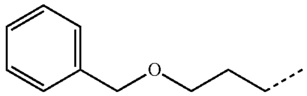 | H | |
| 6 | B2.a | $CH_3$ | H | 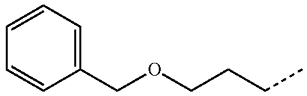 | 5-$OCH_3$ | |
TABLE 1c
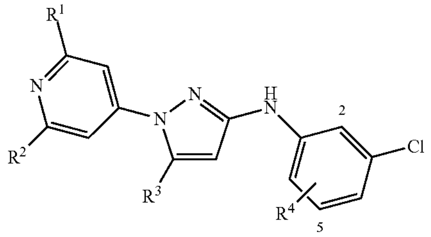
| Co. No. | Pr. | $R^1$ | $R^2$ | $R^3$ | $R^4$ | Stereochemistry and salt forms |
|---|---|---|---|---|---|---|
| 52 | B1.b | $CH_3$ | H | $CH_2OH$ | 2-F | |
| 53 | B1.b | $CH_3$ | $CH_3$ | $CH_2OH$ | 2-F | |
| 54 | B1.b | $CH_3$ | H | $CH_2OH$ | 5-$OCH_3$ | |
| 55 | B2.b | $CH_3$ | H | 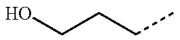 | 2-F | |
| 56 | B2.b | $CH_3$ | H | 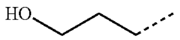 | 5-$OCH_3$ | |
| 57 | B5 | $CH_3$ | H | 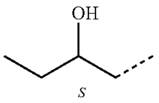 | H | S-enantiomer |
| 58 | B5 | $CH_3$ | H | 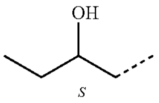 | 2-F | S-enantiomer |
| 59 | B5 | $CH_3$ | H | 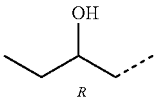 | 2-F | R-enantiomer |
| 60 | B5 | $CH_3$ | H | 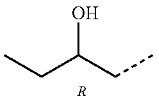 | 5-F | R-enantiomer |

TABLE 1c-continued
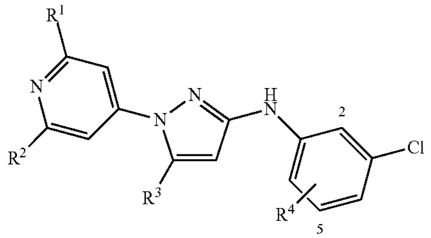
| Co. No. | Pr. | $R^1$ | $R^2$ | $R^3$ | $R^4$ | Stereochemistry and salt forms |
|---|---|---|---|---|---|---|
| 61 | B5 | $CH_3$ | H | 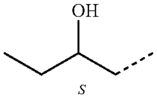 | 5-$OCH_3$ | S-enantiomer |
| 62 | B5 | $CH_3$ | H | 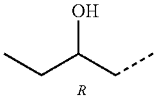 | 5-$OCH_3$ | R-enantiomer |
| 63 | B1.c | $CH_3$ | H | 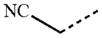 | 2-F | |
| 64 | B1.c | $CH_3$ | $CH_3$ | 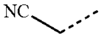 | 2-F | |
| 65 | B1.c | $CH_3$ | H | 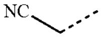 | 5-$OCH_3$ | |
| 66 | B1.d | $CH_3$ | H | 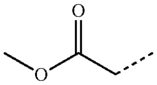 | 2-F | |
| 67 | B1.d | $CH_3$ | $CH_3$ | 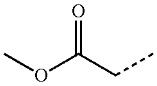 | 2-F | |
| 68 | B1.d | $CH_3$ | H | 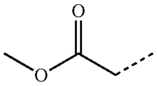 | 5-$OCH_3$ | |
| 69 | B2.c | $CH_3$ | H | 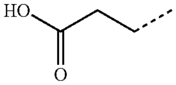 | 2-F | |
| 70 | B2.c | $CH_3$ | H | 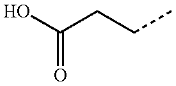 | 5-$OCH_3$ | |
| 71 | B1.e | $CH_3$ | H | 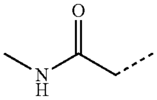 | 2-F | |
| 72 | B1.e | $CH_3$ | H | 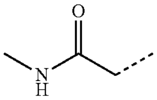 | 5-$OCH_3$ | |
| 73 | B1.e | $CH_3$ | H | 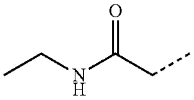 | 2-F | |

TABLE 1c-continued
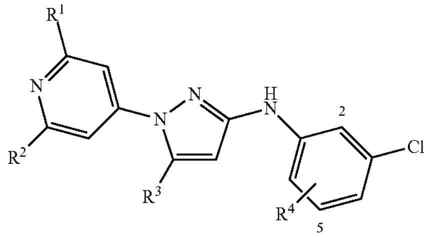
| Co. No. | Pr. | $R^1$ | $R^2$ | $R^3$ | $R^4$ | Stereochemistry and salt forms |
|---|---|---|---|---|---|---|
| 74 | B1.e | $CH_3$ | H | 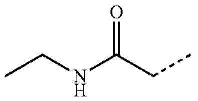 | 5-$OCH_3$ | |
| 75 | B1.e | $CH_3$ | H | 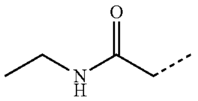 | 2-F | |
| 76 | B1.e | $CH_3$ | H | 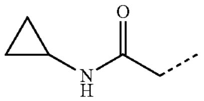 | 2-F | |
| 77 | B1.e | $CH_3$ | H | 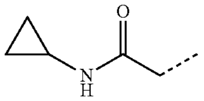 | 5-$OCH_3$ | |
| 78 | B1.e | $CH_3$ | $CH_3$ | 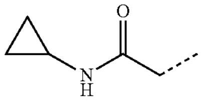 | 2-F | |
| 79 | B1.e | $CH_3$ | H | 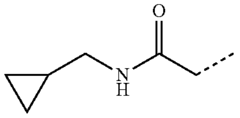 | 2-F | |
| 80 | B1.e | $CH_3$ | $CH_3$ | 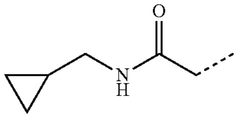 | 2-F | |
| 81 | B1.e | $CH_3$ | H | 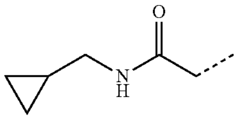 | 5-$OCH_3$ | |
| 82 | B1.e | $CH_3$ | H | 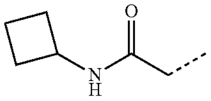 | 2-F | |
| 83 | B1.e | $CH_3$ | H | 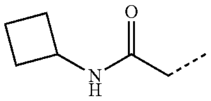 | 5-$OCH_3$ | |
| 84 | B2.d | $CH_3$ | H | 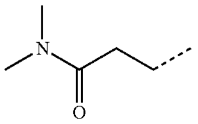 | 2-F | |

TABLE 1c-continued
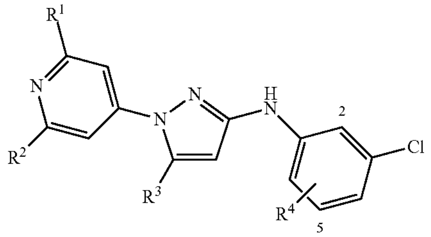
| Co. No. | Pr. | $R^1$ | $R^2$ | $R^3$ | $R^4$ | Stereochemistry and salt forms |
|---|---|---|---|---|---|---|
| 85 | B2.d | $CH_3$ | H | 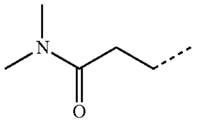 | 5-$OCH_3$ | |
| 86 | B1.a | $CH_3$ | H | 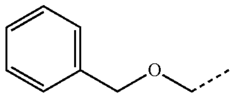 | 2-F | |
| 87 | B1.a | $CH_3$ | $CH_3$ | 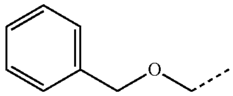 | 2-F | |
| 88 | B1.a | $CH_3$ | H | 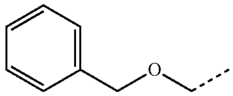 | 5-$OCH_3$ | |
| 89 | B2.a | $CH_3$ | H | 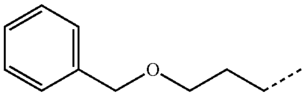 | 2-F | |
| 90 | B2.a | $CH_3$ | H | 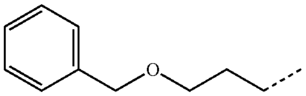 | 5-$OCH_3$ | |
TABLE 1d
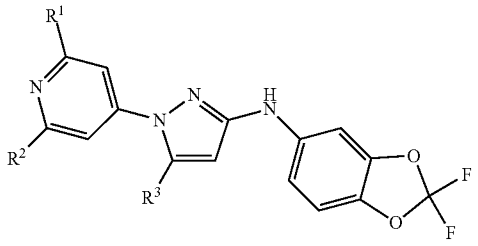
| Co. No. | Pr. | $R^1$ | $R^2$ | $R^3$ | Stereo-chemistry and salt forms |
|---|---|---|---|---|---|
| 91 | B1.b | $CH_3$ | H | $CH_2OH$ | |
| 92 | B2.b | $CH_3$ | H | 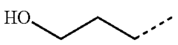 | |
TABLE 1d-continued
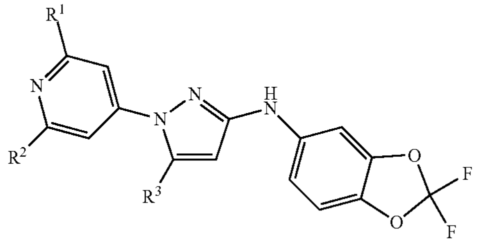
| Co. No. | Pr. | $R^1$ | $R^2$ | $R^3$ | Stereo-chemistry and salt forms |
|---|---|---|---|---|---|
| 93 | B5 | $CH_3$ | H | 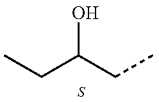 | S-enan-tiomer |
| 94 | B1.c | $CH_3$ | H | 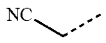 | |

TABLE 1d-continued

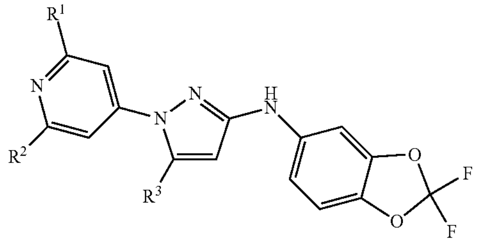

| Co. No. | Pr. | $R^1$ | $R^2$ | $R^3$ | Stereo-chemistry and salt forms |
|---|---|---|---|---|---|
| 95 | B2.c | $CH_3$ | H | 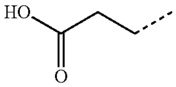 | |
| 96 | B1.d | $CH_3$ | H | 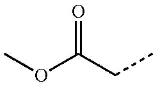 | |
| 97 | B1.e | $CH_3$ | H | 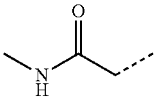 | |
| 98 | B1.e | $CH_3$ | H | 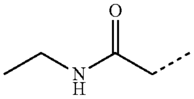 | |
| 99 | B2.d | $CH_3$ | H | 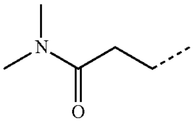 | |
| 100 | B1.e | $CH_3$ | H | 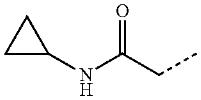 | |
| 101 | B1.e | $CH_3$ | H | 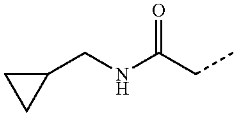 | |
| 102 | B1.e | $CH_3$ | H | 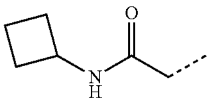 | |
| 103 | B1.a | $CH_3$ | H | 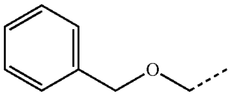 | |
| 104 | B2.a | $CH_3$ | H | 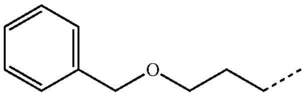 | |

TABLE 1e

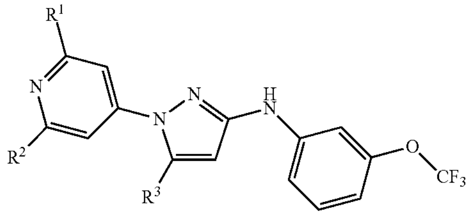

| Co. No. | Pr. | $R^1$ | $R^2$ | $R^3$ | Stereo-chemistry and salt forms |
|---|---|---|---|---|---|
| 105 | B1.b | $CH_3$ | H | $CH_2OH$ | |
| 106 | B5 | $CH_3$ | H | 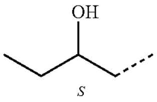 | S-enantiomer |
| 107 | B1.c | $CH_3$ | H | 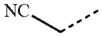 | |
| 108 | B1.c | $CH_3$ | $CH_3$ | 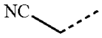 | |
| 109 | B1.d | $CH_3$ | H | 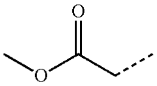 | |
| 110 | B1.d | $CH_3$ | $CH_3$ | 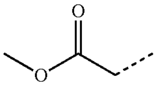 | |
| 111 | B1.e | $CH_3$ | H | 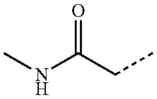 | |
| 112 | B1.e | $CH_3$ | $CH_3$ | 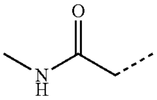 | |
| 113 | B1.e | $CH_3$ | H | 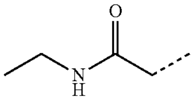 | |
| 114 | B1.e | $CH_3$ | $CH_3$ | 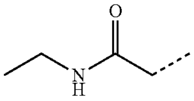 | |
| 115 | B1.e | $CH_3$ | H | 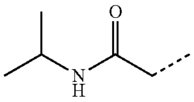 | |
| 116 | B1.e | $CH_3$ | $CH_3$ | 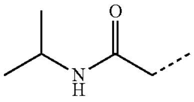 | |
| 117 | B1.e | $CH_3$ | H | 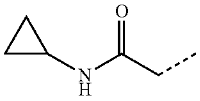 | |

TABLE 1e-continued

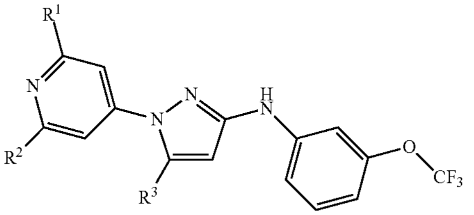

| Co. No. | Pr. | $R^1$ | $R^2$ | $R^3$ | Stereo-chemistry and salt forms |
|---|---|---|---|---|---|
| 118 | B1.e | $CH_3$ | $CH_3$ | 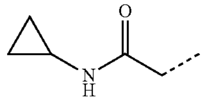 | |
| 119 | B1.e | $CH_3$ | H | 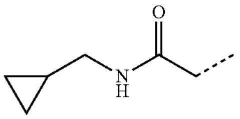 | |
| 120 | B1.e | $CH_3$ | $CH_3$ | 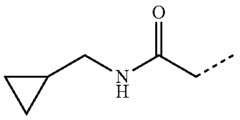 | |
| 121 | B1.e | $CH_3$ | H | 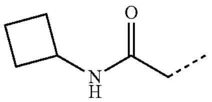 | |
| 122 | B1.a | $CH_3$ | H | 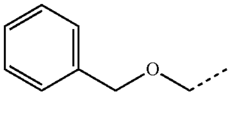 | |
| 123 | B1.a | $CH_3$ | $CH_3$ | 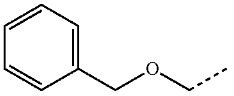 | |

TABLE 1f

| Co. No. | Pr. | Structure | Stereochemistry and salt forms |
|---|---|---|---|
| 124 | B5 | 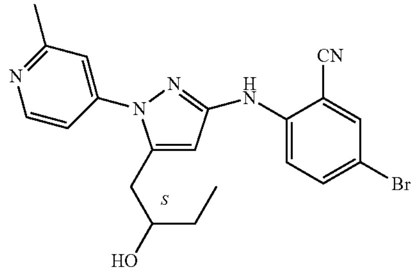 | S-enantiomer |

Analytical Part

LCMS (Liquid Chromatography/Mass Spectrometry)

General Procedure A

The LC measurement was performed using an Acquity HPLC (Ultra Performance Liquid Chromatography) (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds (sec) using a dwell time of 0.02 sec. The capillary needle voltage was 3.5 kV and the source temperature was maintained at 140° C. $N_2$ was used as the nebulizer gas. Data acquisition was performed with a Waters-Micromass MassLynx-Openlynx data system.

General Procedure B

The HPLC measurement was performed using an Alliance HT 2790 (Waters) system comprising a quaternary pump with degasser, an autosampler, a column oven (set at 45° C., unless otherwise indicated), a DAD and a column as specified in the respective methods below. Flow from the column was split to a MS spectrometer. The MS detector was configured with an electrospray ionization source. Mass spectra were acquired by scanning from 100 to 1000 in 1 sec using a dwell time of 0.1 sec. The capillary needle voltage was 3 kV and the source temperature was maintained at 140° C. $N_2$ was used as the nebulizer gas. Data acquisition was performed with a Waters-Micromass MassLynx-Openlynx data system.

LCMS Method 1

In addition to general procedure A: Reversed phase HPLC was carried out on a bridged ethylsiloxane/silica hybrid (BEH) C18 column (1.7 μm, 2.1×50 mm; Waters Acquity) with a flow rate of 0.8 ml/min. 2 Mobile phases (25 mM $NH_4OAc$ in $H_2O/CH_3CN$ 95/5; mobile phase B: $CH_3CN$) were used to run a gradient condition from 95% A and 5% B to 5% A and 95% B in 1.3 minutes (min) and hold for 0.3 min. An injection volume of 0.5 μl was used. Cone voltage was 10 V for positive ionization mode and 20 V for negative ionization mode.

LCMS Method 2

In addition to general procedure A: Reversed phase HPLC was carried out on a BEH C18 column (1.7 μm, 2.1×50 mm; Waters Acquity) with a flow rate of 0.8 ml/min. 2 Mobile phases (mobile phase A: 0.1% formic acid in $H_2O$/MeOH 95/5; mobile phase B: MeOH) were used to run a gradient condition from 95% A and 5% B to 5% A and 95% B in 1.3 min and hold for 0.2 min. An injection volume of 0.5 μl was used. Cone voltage was 10 V for positive ionization mode and 20 V for negative ionization mode.

LCMS Method 3

In addition to general procedure B: Reversed phase HPLC was carried out on an Atlantis C18 column (3.5 μm, 4.6×100 mm) with a flow rate of 1.6 ml/min. 2 Mobile phases (mobile phase A: 70% MeOH+30% $H_2O$; mobile phase B: 0.1% formic acid in $H_2O$/MeOH 95/5) were employed to run a gradient condition from 100% B to 5% B+95% A in 9 min and hold these conditions for 3 min. An injection volume of 10 µl was used. Cone voltage was 10 V for positive ionization mode and 20 V for negative ionization mode.

LCMS Method 4

In addition to general procedure B: Column heater was set at 60° C. Reversed phase HPLC was carried out on an Xterra MS C18 column (3.5 µm, 4.6×100 mm) with a flow rate of 1.6 ml/min. Three mobile phases (mobile phase A: 95% 25 mM $NH_4OAc$+5% $CH_3CN$; mobile phase B: $CH_3CN$; mobile phase C: MeOH) were employed to run a gradient condition from 100% A to 50% B and 50% C in 6.5 min, to 100% B in 0.5 min and hold these conditions for 1 minute and reequilibrate with 100% A for 1.5 min. An injection volume of 10 µl was used. Cone voltage was 10 V for positive ionization mode and 20 V for negative ionization mode.

LCMS Method 5

In addition to general procedure B: Column heater was set at 40° C. Reversed phase HPLC was carried out on an Xterra MS C18 column (3.5 µm, 4.6×100 mm) with a flow rate of 1.6 ml/min. Three mobile phases (mobile phase A: 95% 25 mM $NH_4OAc$+5% $CH_3CN$; mobile phase B: $CH_3CN$; mobile phase C: MeOH) were employed to run a gradient condition from 100% A to 1% A, 49% B and 50% C in 6.5 min, to 1% A and 99% B in 1 min and hold these conditions for 1 min and reequilibrate with 100% A for 1.5 min. An injection volume of 10 µl was used. Cone voltage was 10 V for positive ionization mode and 20 V for negative ionization mode.

Melting Points

For a number of compounds, melting points (m.p.) were determined with a DSC823e (Mettler-Toledo). Melting points were measured with a temperature gradient of 30° C./min. Maximum temperature was 400° C. Values are peak values.

The results of the analytical measurements are shown in table 2.

TABLE 2

Retention time ($R_t$) in min., $[M+H]^+$ peak (protonated molecule), LCMS method and m.p. (melting point in ° C.).

| Co. No. | $R_t$ | $[M+H]^+$ | LCMS Method | m.p. (° C.) |
|---|---|---|---|---|
| 1 | 6.32 | 469 | 4 | 148.1 |
| 2 | 5.25 | 379 | 4 | n.d. |
| 3 | 5.44 | 388 | 4 | 183.8 |
| 4 | 5.54 | 421 | 4 | n.d. |
| 5 | 5.42 | 460 | 4 | 228.3 |
| 6 | 1.29 | 497 | 2 | n.d. |
| 7 | 0.97 | 407 | 1 | n.d. |
| 8 | 0.77 | 421 | 1 | n.d. |
| 9 | 5.42 | 448 | 4 | 146.4 |
| 10 | 6.42 | 359 | 3 | 164.7 |
| 11 | 1.07 | 405 | 1 | n.d. |
| 12 | 0.76 | 391 | 1 | n.d. |
| 13 | 5.68 | 377 | 5 | 144.4 |
| 14 | 5.23 | 301 | 4 | 169.2 |
| 15 | 5.82 | 317 | 3 | 155.3 |
| 16 | 4.80 | 345 | 4 | n.d. |
| 17 | 0.95 | 359 | 1 | 163.2 |
| 18 | 0.99 | 377 | 1 | 149.1 |
| 19 | 6.97 | 377 | 3 | 170.4 |
| 20 | 1.02 | 377 | 1 | n.d. |
| 21 | 0.98 | 377 | 1 | 166.6 |
| 22 | 5.33 | 331 | 4 | 184.2 |
| 23 | n.d. | n.d. | — | n.d. |
| 24 | n.d. | n.d. | — | n.d. |
| 25 | n.d. | n.d. | — | n.d. |
| 26 | n.d. | n.d. | — | n.d. |

TABLE 2-continued

Retention time ($R_t$) in min., $[M+H]^+$ peak (protonated molecule), LCMS method and m.p. (melting point in ° C.).

| Co. No. | $R_t$ | $[M+H]^+$ | LCMS Method | m.p. (° C.) |
|---|---|---|---|---|
| 27 | 4.47 | 358 | 4 | 252.9 |
| 28 | 4.66 | 372 | 4 | 242.4 |
| 29 | 4.53 | 398 | 4 | 230.3 |
| 30 | 6.17 | 386 | 3 | n.d. |
| 31 | 7.51 | 407 | 3 | 171.0 |
| 32 | 6.66 | 435 | 5 | 108.2 |
| 33 | 0.94 | 349 | 1 | n.d. |
| 34 | 1.01 | 377 | 2 | n.d. |
| 35 | 7.05 | 391 | 3 | 170.0 |
| 36 | 7.28 | 421 | 3 | n.d. |
| 37 | 1.04 | 391 | 1 | 169.5 |
| 38 | 0.99 | 421 | 1 | 129.0 |
| 39 | 1.10 | 421 | 2 | 129.2 |
| 40 | 1.02 | 358 | 1 | n.d. |
| 41 | n.d. | n.d. | — | n.d. |
| 42 | 0.98 | 390 | 2 | |
| 43 | 0.92 | 420 | 1 | 237.9 |
| 44 | 0.94 | 404 | 1 | 228.9 |
| 45 | 5.19 | 434 | 4 | 248.6 |
| 46 | 5.21 | 446 | 4 | 251.3 |
| 47 | 1.07 | 430 | 2 | 207.5 |
| 48 | 5.46 | 460 | 4 | 249.2 |
| 49 | 6.79 | 418 | 3 | n.d. |
| 50 | n.d. | n.d. | — | n.d. |
| 51 | 1.26 | 467 | 2 | n.d. |
| 52 | 0.93 | 333 | 1 | n.d. |
| 53 | n.d. | n.d. | — | n.d. |
| 54 | n.d. | n.d. | — | n.d. |
| 55 | 0.96 | 361 | 1 | n.d. |
| 56 | 0.91 | 373 | 1 | n.d. |
| 57 | 0.98 | 357 | 1 | 149.3 |
| 58 | 1.02 | 375 | 1 | 168.2 |
| 59 | 6.87 | 375 | 3 | 168.1 |
| 60 | 7.18 | 375 | 3 | 182.4 |
| 61 | 0.99 | 387 | 1 | 125.3 |
| 62 | 6.91 | 387 | 3 | 121.9 |
| 63 | 1.05 | 342 | 2 | n.d. |
| 64 | 1.06 | 356 | 1 | n.d. |
| 65 | n.d. | n.d. | — | n.d. |
| 66 | n.d. | n.d. | — | n.d. |
| 67 | n.d. | n.d. | — | n.d. |
| 68 | n.d. | n.d. | — | n.d. |
| 69 | n.d. | n.d. | — | n.d. |
| 70 | n.d. | n.d. | — | n.d. |
| 71 | 0.93 | 374 | 2 | 229.7 |
| 72 | 0.94 | 386 | 2 | 215.0 |
| 73 | 0.98 | 388 | 2 | 205.1 |
| 74 | 0.98 | 400 | 2 | 224.0 |
| 75 | 0.96 | 402 | 1 | n.d. |
| 76 | 0.93 | 400 | 1 | 192.6 |
| 77 | 0.99 | 412 | 2 | n.d. |
| 78 | 0.96 | 414 | 1 | 222.9 |
| 79 | 0.99 | 414 | 1 | 220.5 |
| 80 | 1.02 | 428 | 1 | 210.4 |
| 81 | 1.04 | 426 | 2 | 248.7 |
| 82 | 1.00 | 414 | 1 | 223.2 |
| 83 | 1.05 | 426 | 2 | 236.4 |
| 84 | 5.31 | 402 | 4 | n.d. |
| 85 | 1.01 | 414 | 2 | n.d. |
| 86 | n.d. | n.d. | — | n.d. |
| 87 | 1.27 | 437 | 1 | n.d. |
| 88 | n.d. | n.d. | — | n.d. |
| 89 | 1.31 | 451 | 1 | n.d. |
| 90 | 1.25 | 463 | 1 | n.d. |
| 91 | 0.94 | 361 | 1 | n.d. |
| 92 | 5.21 | 389 | 4 | 163.3 |
| 93 | 1.03 | 403 | 1 | 138.3 |
| 94 | 1.03 | 370 | 1 | n.d. |
| 95 | 4.57 | 403 | 4 | n.d. |
| 96 | n.d. | n.d. | — | n.d. |
| 97 | 0.91 | 402 | 1 | 271.2 |
| 98 | 0.94 | 416 | 1 | 239.2 |
| 99 | 5.36 | 430 | 4 | 132.0 |
| 100 | 1.02 | 428 | 2 | 248.9 |

TABLE 2-continued

| Retention time ($R_t$) in min., $[M + H]^+$ peak (protonated molecule), LCMS method and m.p. (melting point in ° C.). | | | | |
|---|---|---|---|---|
| Co. No. | $R_t$ | $[M + H]^+$ | LCMS Method | m.p. (° C.) |
| 101 | 1.10 | 442 | 2 | 232.3 |
| 102 | 1.08 | 442 | 2 | 237.7 |
| 103 | 1.23 | 451 | 1 | n.d. |
| 104 | 8.23 | 479 | 3 | 124.4 |
| 105 | 5.26 | 365 | 4 | n.d. |
| 106 | 1.05 | 407 | 1 | 147.3 |
| 107 | 5.45 | 374 | 4 | 180.2 |
| 108 | 1.10 | 388 | 2 | n.d. |
| 109 | 6.95 | 407 | 3 | 115.8 |
| 110 | n.d. | n.d. | — | n.d. |
| 111 | 6.52 | 406 | 3 | 231.5 |
| 112 | 1.02 | 420 | 2 | 222.0 |
| 113 | 6.70 | 420 | 3 | 210.3 |
| 114 | 1.05 | 434 | 2 | 224.2 |
| 115 | 6.90 | 434 | 3 | 228.3 |
| 116 | 5.53 | 448 | 4 | 229.1 |
| 117 | 1.04 | 432 | 2 | 224.6 |
| 118 | 1.05 | 446 | 2 | 230.8 |
| 119 | 6.95 | 446 | 3 | 191.7 |
| 120 | 1.09 | 460 | 2 | 199.4 |
| 121 | 7.02 | 446 | 3 | 227.7 |
| 122 | 6.32 | 455 | 4 | 139.8 |
| 123 | n.d. | n.d. | — | n.d. |
| 124 | 1.01 | 426 | 1 | n.d. |

(n.d. means not determined)

Optical Rotation

The optical rotation was measured using a Perkin Elmer 341 polarimeter. $[\alpha]_D^{20}$ indicates the optical rotation measured with light at the wavelength of the D-line of sodium (589 nm) at a temperature of 20° C. The cell pathlength is 1 dm. Behind the actual value the concentration and solvent of the solution which was used to measure the optical rotation are mentioned. The results are shown in Table 3.

TABLE 3

| Comp. No. | $[\alpha]_D^{20}$ | concentration | solvent |
|---|---|---|---|
| 19 | −11.23° | 0.2938 w/v % | MeOH |
| 59 | −9.69° | 0.3510 w/v % | MeOH |
| 13 | −8.09° | 0.3338 w/v % | MeOH |
| 36 | −7.88° | 0.3682 w/v % | MeOH |
| 62 | −8.73° | 0.4468 w/v % | MeOH |
| 60 | −10.64° | 0.4134 w/v % | MeOH |

NMR

For a number of compounds, $^1H$ NMR spectra were recorded on a Bruker DPX-360 or on a Bruker DPX-400 spectrometer with standard pulse sequences, operating at 360 MHz and 400 MHz respectively, using DMSO-$d_6$ (deuterated DMSO, dimethyl-d6 sulfoxide) as solvent. Chemical shifts (δ) are reported in parts per million (ppm) relative to tetramethylsilane (TMS), which was used as internal standard.

Compound 1: $^1H$ NMR (360 MHz) δ ppm 2.50 (s, 3 H) 3.83 (s, 3 H) 4.62 (s, 2 H) 4.72 (s, 2 H) 6.29 (s, 1 H) 6.67 (t, J=1.8 Hz, 1 H) 7.28-7.40 (m, 5 H) 7.42 (t, J=1.8 Hz, 1 H) 7.44-7.49 (m, 2 H) 7.54 (d, J=1.8 Hz, 1 H) 8.49 (d, J=5.9 Hz, 1 H) 9.38 (s, 1 H).

Compound 3: $^1H$ NMR (360 MHz) δ ppm 2.54 (s, 3 H) 3.83 (s, 3 H) 4.54 (s, 2 H) 6.23 (s, 1 H) 6.68 (s, 1 H) 7.39 (s, 1 H) 7.42 (dd, J=5.5, 2.2 Hz, 1 H) 7.46 (t, J=2.2 Hz, 1 H) 7.48 (d, J=1.8 Hz, 1 H) 8.55 (d, J=5.5 Hz, 1 H) 9.39 (s, 1 H).

Compound 5: $^1H$ NMR (360 MHz) δ ppm 0.09-0.17 (m, 2 H) 0.36-0.43 (m, 2 H) 0.75-0.96 (m, 1 H) 2.51 (s, 3 H) 2.94 (t, J=6.2 Hz, 2 H) 3.79 (s, 2 H) 3.82 (s, 3 H) 6.11 (s, 1 H) 6.65 (t, J=1.8 Hz, 1 H) 7.39 (s, 1 H) 7.43 (dd, J=5.5, 2.2 Hz, 1 H) 7.45-7.48 (m, 2 H) 8.28 (t, J=5.7 Hz, 1 H) 8.49 (d, J=5.9 Hz, 1 H) 9.28 (s, 1 H).

Compound 7: $^1H$ NMR (400 MHz) δ ppm 1.73-1.82 (m, 2 H) 2.52 (s, 3 H) 2.89 (t, J=7.7 Hz, 2 H) 3.47 (t, J=6.2 Hz, 2 H) 3.82 (s, 3 H) 5.99 (s, 1 H) 6.63 (t, J=1.8 Hz, 1 H) 7.36-7.42 (m, 2 H) 7.43-7.49 (m, 2 H) 8.49 (d, J=5.9 Hz, 1 H) 9.21 (s, 1 H).

Compound 9: $^1H$ NMR (360 MHz) δ ppm 2.53 (s, 3 H) 2.73 (t, J=7.1 Hz, 2 H) 2.82 (s, 3 H) 2.99 (s, 3 H) 3.05 (t, J=7.1 Hz, 2 H) 3.81 (s, 3 H) 6.00 (s, 1 H) 6.64 (t, J=1.8 Hz, 1 H) 7.37 (t, J=1.8 Hz, 1 H) 7.42 (dd, J=5.5, 2.2 Hz, 1 H) 7.45 (t, J=1.8 Hz, 1 H) 7.49 (d, J=2.2 Hz, 1 H) 8.52 (d, J=5.5 Hz, 1 H) 9.24 (s, 1 H).

Compound 10: $^1H$ NMR (400 MHz) δ ppm 0.86 (t, J=7.5 Hz, 3 H) 1.27-1.52 (m, 2 H) 2.53 (s, 3 H) 2.75-2.98 (m, 2 H) 3.57-3.71 (m, 1 H) 4.78 (d, J=5.5 Hz, 1 H) 6.04 (s, 1 H) 7.09-7.20 (m, 1 H) 7.21-7.35 (m, 1 H) 7.43 (dd, J=5.5, 1.8 Hz, 1 H) 7.48 (d, J=1.8 Hz, 1 H) 7.61 (ddd, J=13.9, 7.1, 2.7 Hz, 1 H) 8.50 (d, J=5.5 Hz, 1 H) 9.01 (s, 1 H).

Compound 13: $^1H$ NMR (360 MHz) δ ppm 0.86 (t, J=7.3 Hz, 3 H) 1.27-1.52 (m, 2 H) 2.53 (s, 3 H) 2.73-2.97 (m, 2 H) 3.53-3.68 (m, 1 H) 4.81 (d, J=5.9 Hz, 1 H) 6.18 (s, 1 H) 7.12-7.30 (m, 1 H) 7.44 (dd, J=5.7, 1.6 Hz, 1 H) 7.49 (d, J=1.6 Hz, 1 H) 7.97-8.15 (m, 1 H) 8.49 (d, J=5.5 Hz, 1 H) 8.81 (s, 1 H).

D. Pharmacological Examples

Example D.1

$Ca^{2+}$ Flux Imaging (FDSS)

Materials a) Assay Buffer

Hanks buffered saline solution (HBSS, Invitrogen, Belgium), supplemented with 10 mM HEPES (Invitrogen, Belgium), $CaCl_2$ to a final concentration of 5 mM, 0.1% Bovine serum albumin (Sigma-Aldrich NV, Belgium).

b) Calcium-Sensitive Dye—Fluo-4AM

Fluo-4AM (Molecular Probes, USA) was dissolved in DMSO containing 10% Pluronic acid (Molecular Probes, USA) to give a stock solution which was diluted in assay buffer supplemented with 5 mM probenicid (Sigma, Aldrich NV, Belgium) to give a final concentration of 2 μM.

c) 384-Well Plates

Black 384 well plate black/clear plates, PDL pre-coated (Corning, Incorporated, USA)

d) Calcium Flux Measurement

A Functional drug screening system (FDSS, Hamamatsu) was used to measure intracellular free-calcium flux signals.

Method

Monolayers of hα7-wt nAChR-expressing cells were grown in multi-well plates, in particular black-sided, transparent bottomed 384 well plates coated with poly-D-lysine for 24 hours prior to loading with a fluorescent calcium indicator, in a particular embodiment loading with fluo-4AM for up to 120 minutes.

PAM activity was detected in real time by applying the compounds to be tested to the loaded cells along with a α7 nicotinic receptor agonist during constant monitoring of cellular fluorescence in a FDSS. Compounds giving peak fluorescent responses greater than the response due to agonist alone, were considered to be α7 nAChR PAM's. In a particular embodiment, the α7 nicotinic receptor agonist was choline, a more particular embodiment choline applied at a submaximal concentration of 100 μM. In a further setting of the present invention the compounds to be tested were applied prior to the α7 nicotinic receptor agonist, in a particular embodiment up to 10 minutes prior to the agonist.

A control response to choline was calculated on each plate from the difference in peak in fluorescence in wells receiving either choline or assay buffer alone. Compounds of the present invention were tested at a concentration range from 0.01 μM to 30 μM. Compounds were considered to have an interesting activity when they potentiated the choline signal at least with 200% when tested at a concentration of 30 μM (the efficacy of 100 μM choline was defined as 100% in the absence of a PAM). An $EC_{50}$ (or $pEC_{50}$) was determined as a concentration relating to half the maximal effect, when a clear sigmoidal curve with top plateau was obtained. The $EC_{50}$ (or $pEC_{50}$) was defined as lower than maximal concentration in case the compound activity did not reach a top plateau at maximal concentration (indicated in table 4 as "<5")

The compounds also have a potentiating effect on the response to choline when measured by whole-cell patch clamp electrophysiology in GH4C1 cells stably over-expressing the human wild-type α7 receptor.

Example D.2

Patch-Clamp Current Recording

Patch-clamp recording from mammalian cells has provided a powerful means of assessing the function of membrane-bound proteins thought to be subunits of ligand-gated ion channels. Activation of such proteins by endogenous or exogenous ligands cause opening of a pore associated with the receptor through which ions flow down their electrochemical gradient. In the case of the hα7-wt nAChR-expressing GH4C1 recombinant cell line the preferential permeability to calcium of this receptor means that calcium flows into the cell upon activation by ACh, choline and other nicotinic ligands giving rise to a calcium current. Since this receptor rapidly desensitizes in the presence of agonist it is important an application system is used which is capable of very rapid switching of solutions (<100 ms) to prevent partial or full desensitisation of receptor responses coincident with the time of agonist application. Consequently, a second convenient technique to assess the enhancement of nicotinic efficacy is patch-clamp recording from hα7-wt nAChR-expressing GH4C1 cells coupled with a rapid-application system.

Materials a) Assay Buffers

The external recording solution consisted of 152 mM NaCl, 5 mM KCl, 1 mM $MgCl_2$, 1 mM Calcium, 10 mM HEPES; pH 7.3. The internal recording solution consisted of 140 mM CsCl, 10 mM HEPES, 10 mM EGTA, 1 mM $MgCl_2$, pH 7.3.

b) Patch-clamp recording was carried out using a Patch-clamp amplifier (Multiclamp 700A, Axon Instruments, CA, USA). hα7-wt nAChR-expressing GH4C1 cells were patch-clamp in the whole cell configuration (Hamill et al, 1981) with a borosilicate glass electrode of 1.5-3 MΩ tip resistance when filled with the internal recording solution. Recordings were made on cells with membrane resistance >500 MΩ and more preferably 1 GΩ and series resistance <15 MΩ with at least 60% series resistance compensation. Membrane potential was clamped at −70 mV.

c) Agonists

ACh, choline, were purchased from Sigma-Aldrich NV, Belgium.

d) Compound Application

A 16-channel Dynflow DF-16 microfluidics system (Cellectricon, Sweden) for rapid switching of solutions (switching resolution time <100 ms) was used to apply control, agonist and PAM compounds to hα7-wt nAChR-expressing GH4C1 cells.

Method hα7-wt nAChR-expressing GH4C1 cells were plated in external recording solution in the Dynaflow perfusion chamber and were allowed to settle for up to 20 minutes. Individual cells were whole-cell patched and gently lifted off the chamber bottom with the patch pipette into a continuously-flowing perfusion stream (12 μl/min) of external recording solution. PAM activity was detected in real time by pre-applying the compounds to be tested to the loaded cells followed by an α7 nicotinic receptor agonist during constant monitoring of cellular membrane current. Compounds giving current responses greater than the response due to agonist alone, were considered to be α7 nAChR PAM's. In a particular embodiment, the α7 nicotinic receptor agonist was activated by a non-selective nicotinic agonist, in a more particular embodiment the agonist was choline, and an even more particular embodiment choline applied at a sub-maximal concentration of 1 mM. In a further setting of the present invention the compounds to be tested were applied prior to the α7 nicotinic receptor agonist, in a more particular embodiment up to 30 seconds prior to the agonist and even more particularly 5 seconds prior to the agonist. A control response was calculated from the area under the curve of the current elicited in each cell to an application of submaximal choline for 250 ms. Area under the curve is the integration of net current over time and is a common representation of the total ion flux through the channel. Increases in agonist efficacy elicited by a positive allosteric modulator were calculated as percent potentiation of "area under curve" (AUC) of the agonist response. Potentiation greater than control AUC caused by compounds of the invention indicates that they are expected to have useful therapeutic activity. $EC_{50}$ values (potency), maximal effect (% efficacy), and Hill slopes were estimated by fitting the data to the logistic equation using GraphPad Prism (GraphPad Software, Inc., San Diego, Calif.).

TABLE 4

Potency ($pEC_{50}$) and % efficacy for a number of compounds.

| Co. No. | pEC50 | % Efficacy | PAM type | Co. No. | pEC50 | % Efficacy | PAM type |
|---|---|---|---|---|---|---|---|
| 14 | 5.47 | 1972 | n.d. | | | @30 μM | |
| 31 | 5.94 | 2728 | 0 | 24 | n.d. | n.d. | n.d. |
| 15 | 5.55 | 1007 | n.d. | 17 | 5.78 | 879.5 | 2 |
| 10 | 6.08 | 1479 | 2 | 28 | 5.60 | 1377 | 2 |
| 35 | 6.16 | 1858 | 2 | 29 | 6.16 | 1279 | 2 |
| 22 | 5.72 | 963 | 0 | 32 | 5.99 | 1551 | n.d. |
| 23 | n.d. | n.d. | n.d. | 93 | 5.77 | 2213 | 2 |
| 37 | 5.64 | 3107 | 2 | 39 | 6.03 | 2913 | 4 |
| 26 | n.d. | n.d. | n.d. | 18 | 5.62 | 2582 | 1 |
| 27 | n.d. | 1419 | n.d. | 106 | 5.74 | 1765 | 2 |
| 38 | 5.88 | 1808 | 2 | 11 | n.d. | n.d. | n.d. |
| 57 | 5.65 | 1987 | 2 | 12 | n.d. | n.d. | n.d. |
| 61 | 6.10 | 2630 | 2 | 2 | n.d. | n.d. | n.d. |
| 124 | 5.78 | 1711 | 2 | 3 | 5.71 | 930 | n.d. |
| 21 | 5.46 | 2056 | 2 | 98 | 5.92 | 2011 | 2 |
| 58 | 5.60 | 2644 | 1 | 85 | 6.53 | 1964 | 4 |
| 104 | 6.25 | 2531 | n.d. | 4 | n.d. | n.d. | n.d. |
| 16 | n.d. | n.d. | n.d. | 43 | 6.25 | 1594 | 4 |
| 25 | n.d. | n.d. | n.d. | 89 | n.d. | n.d. | n.d. |
| 86 | n.d. | n.d. | n.d. | 55 | n.d. | n.d. | n.d. |
| 52 | n.d. | n.d. | n.d. | 69 | n.d. | n.d. | n.d. |
| 63 | 5.41 | 433.5 | n.d. | 88 | n.d. | n.d. | n.d. |

TABLE 4-continued

Potency ($pEC_{50}$) and % efficacy for a number of compounds.

| Co. No. | pEC50 | % Efficacy | PAM type | Co. No. | pEC50 | % Efficacy | PAM type |
|---|---|---|---|---|---|---|---|
| 30 | 6.01 | 2872 | 4 | 54 | n.d. | n.d. | n.d. |
| 49 | 6.53 | 3850 | 4 | 65 | n.d. | n.d. | n.d. |
| 7 | 5.54 | 2335 | n.d. | 68 | n.d. | n.d. | n.d. |
| 66 | n.d. | n.d. | n.d. | 45 | 6.70 | 2636 | 4 |
| 51 | n.d. | n.d. | n.d. | 72 | 5.74 | 2466 | 3 |
| 6 | n.d. | n.d. | n.d. | 74 | 6.11 | 2690 | 4 |
| 71 | 5.65 | 1986 | 2 | 81 | 6.83 | 2357 | 0 |
| 73 | 5.90 | 2910 | 3 | 77 | 6.22 | 2615 | 4 |
| 92 | 5.63 | 2239 | 2 | 83 | 6.84 | 2584 | 4 |
| 79 | 6.52 | 2767 | 4 | 5 | 7.12 | 1497 | 4 |
| 103 | n.d. | n.d. | n.d. | 48 | 7.10 | 2102 | 4 |
| 40 | 5.36 | 2895 | n.d. | 122 | 6.43 | 2030 | n.d. |
| 50 | n.d. | n.d. | n.d. | 46 | 6.63 | 2214 | 4 |
| 33 | n.d. | n.d. | n.d. | 90 | n.d. | n.d. | n.d. |
| 9 | 6.77 | 2873 | 4 | 56 | n.d. | n.d. | n.d. |
| 84 | 6.18 | 3956 | 4 | 70 | n.d. | n.d. | n.d. |
| 8 | n.d. | n.d. | n.d. | 100 | 5.90 | 1758 | 2 |
| 41 | n.d. | n.d. | n.d. | 102 | 6.62 | 2003 | 2 |
| 42 | 5.73 | 4002 | 4 | 97 | 5.60 | 1351 | n.d. |
| 44 | 6.22 | 3917 | 2 | 107 | 5.55 | 1646 | n.d. |
| 47 | 6.66 | 3420 | 4 | 109 | 5.70 | 2497 | n.d. |
| 1 | 5.84 | 2336 | n.d. | 105 | n.d. | n.d. | n.d. |
| 99 | 6.31 | 2871 | 4 | 111 | 5.64 | 822 | 2 |
| 76 | 5.96 | 2955 | 3 | 119 | 6.49 | 2120 | 2 |
| 82 | 6.31 | 2962 | 2 | 117 | 5.92 | 2279 | 3 |
| 95 | n.d. | n.d. | n.d. | 113 | 5.94 | 2304 | 3 |
| 91 | n.d. | n.d. | n.d. | 121 | 6.38 | 2154 | 2 |
| 94 | n.d. | n.d. | n.d. | 87 | n.d. | n.d. | n.d. |
| 96 | n.d. | n.d. | n.d. | 53 | n.d. | n.d. | n.d. |
| 101 | 6.22 | 4119 | 2 | 64 | n.d. | n.d. | n.d. |
| 34 | n.d. | n.d. | n.d. | 67 | n.d. | n.d. | n.d. |
| 80 | 7.02 | 2517 | 2 | 116 | 6.61 | 2312 | 2 |
| 75 | 6.43 | 1749 | 2 | 20 | 6.07 | 1243 | 2 |
| 78 | 6.39 | 3420 | 2 | 19 | 6.51 | 705 | n.d. |
| 115 | 6.41 | 1817 | 1 | 59 | 6.16 | 1375 | n.d. |
| 123 | n.d. | n.d. | n.d. | 13 | 6.50 | 1087 | n.d. |
| 108 | n.d. | n.d. | n.d. | 36 | 6.79 | 1284 | 2 |
| 110 | n.d. | n.d. | n.d. | 62 | 6.37 | 1068 | n.d. |
| 112 | 5.89 | 1782 | 2 | 60 | 6.62 | 1252 | n.d. |
| 114 | 6.51 | 1729 | 2 | | | | |
| 120 | 6.85 | 2108 | 2 | | | | |
| 118 | 6.49 | 1673 | 2 | | | | |

The $pEC_{50}$ and % efficacy values are those from the $Ca^{2+}$ assay as described in D.1.

The PAM type is obtained from the patch clamp current recording as described hereinbefore).

Composition Examples

"Active ingredient" (a.i.) as used throughout these examples relates to a compound of formula (I), including any stereochemically isomeric form thereof, a pharmaceutically acceptable salt thereof or a solvate thereof; in particular to any one of the exemplified compounds.

Typical examples of recipes for the formulation of the invention are as follows:

1. Tablets

| | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| | |
|---|---|
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound according to formula (I)

(I)

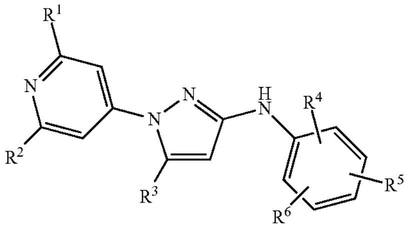

or a stereochemically isomeric form thereof, wherein $R^1$ and $R^2$ each independently represent hydrogen or $C_{1-4}$alkyl;

$R^3$ is $C_{1-6}$alkyl optionally substituted with one or more substituents independently selected from the group consisting of hydroxyl, cyano, $C_{1-6}$alkyloxy, benzyloxy, $R^xR^yN—C(=O)—$, and $R^zO—C(=O)—$;

$R^x$ and $R^y$ each independently represent hydrogen, $C_{1-4}$alkyl, cyclo$C_{3-6}$alkyl or (cyclo$C_{3-6}$alkyl)$C_{1-4}$alkyl;

$R^z$ represents hydrogen or $C_{1-3}$alkyl;

$R^4$, $R^5$ and $R^6$ each independently represent hydrogen, halo, $C_{1-6}$alkyl, cyano, trifluoromethyl, trifluoromethoxy, or methoxy; or $R^4$ and $R^5$ when attached to 2 vicinal carbon atoms together form a bivalent radical of formula $—O—CF_2—O—$; or a pharmaceutically acceptable addition salt thereof.

2. The compound according to claim 1 or a stereoisomeric form thereof, wherein $R^1$ and $R^2$ each independently represent hydrogen or methyl;

$R^3$ is $C_{1-4}$alkyl optionally substituted with one or more substituents independently selected from the group consisting of hydroxyl, cyano, methoxy, benzyloxy, $R^xR^YN—C(=O)—$, and $R^zO—C(=O)—$;

$R^x$ and $R^y$ each independently represent hydrogen, $C_{1-4}$alkyl, cyclo$C_{3-6}$alkyl or (cyclo$C_{3-6}$alkyl)$C_{1-4}$alkyl;

$R^z$ represents hydrogen or $C_{1-3}$alkyl;

$R^4$, $R^5$ and $R^6$ each independently represent hydrogen, halo, cyano, trifluoromethyl, trifluoromethoxy, or methoxy; or $R^4$ and $R^5$ when attached to 2 vicinal carbon atoms together form a bivalent radical of formula —O—$CF_2$—O—; or a pharmaceutically acceptable addition salt thereof.

3. The compound according to claim 1, wherein $R^4$, $R^5$ and $R^6$ each independently represent halo, $C_{1-6}$alkyl, cyano, trifluoromethyl, trifluoromethoxy, or methoxy; or $R^4$ and $R^5$ when attached to 2 vicinal carbon atoms together form a bivalent radical of formula —O—$CF_2$—O—.

4. The compound according to claim 1 or a stereoisomeric form thereof, wherein $R^1$ and $R^2$ each independently represent hydrogen or methyl;

$R^3$ is methyl; hydroxymethyl; hydroxypropyl; (2R)-2-hydroxybutyl; (2S)-2-hydroxybutyl; methoxymethyl; cyanomethyl; carboxymethyl; carboxyethyl; 2-methoxy-2-oxoethyl; 3-methoxy-3-oxopropyl; 2-methylamino-2-oxoethyl; 2-ethylamino-2-oxoethyl; 2-[(cyclopropylmethyl)amino]-2-oxoethyl; 2-(cyclopropylamino)-2-oxoethyl; 2-(cyclobutylamino)-2-oxoethyl; 3-(dimethylamino)-3-oxopropyl; benzyloxymethyl; benzyloxypropyl; or 2-[(1-methylethyl)amino]-2-oxoethyl;

$R^4$, $R^5$ and $R^6$ each independently represent hydrogen, chloro, fluoro, bromo, cyano, trifluoromethyl, trifluoromethoxy, or methoxy; or $R^4$ and $R^5$ when attached to 2 vicinal carbon atoms together form a bivalent radical of formula —O—$CF_2$—O—; or a pharmaceutically acceptable addition salt thereof.

5. The compound according to claim 1 or a stereoisomeric form thereof, wherein at least one of $R^4$, $R^5$ or $R^6$ is other than hydrogen.

6. A pharmaceutical composition comprising a pharmaceutically acceptable carrier and as active ingredient a therapeutically effective amount of a compound as defined in claim 1.

* * * * *